US 9,359,594 B2

(12) United States Patent
Morita et al.

(10) Patent No.: US 9,359,594 B2
(45) Date of Patent: Jun. 7, 2016

(54) ARTIFICIAL BLOOD VESSEL AND METHOD OF MANUFACTURING THEREOF

(71) Applicant: DAI NIPPON PRINTING CO., LTD., Tokyo-to (JP)

(72) Inventors: Ikuo Morita, Tokyo (JP); Hideyuki Miyake, Tokyo-to (JP)

(73) Assignee: DAI NIPPON PRINTING CO., LTD., Tokyo-to (JP)

( * ) Notice: Subject to any disclaimer, the term of this patent is extended or adjusted under 35 U.S.C. 154(b) by 162 days.

(21) Appl. No.: 13/733,363

(22) Filed: Jan. 3, 2013

(65) Prior Publication Data

US 2013/0137156 A1 May 30, 2013

Related U.S. Application Data

(62) Division of application No. 11/597,975, filed as application No. PCT/JP2005/009917 on May 31, 2005, now Pat. No. 8,367,411.

(30) Foreign Application Priority Data

Jun. 1, 2004 (JP) ................. 2004-162900

(51) Int. Cl.
*C12N 5/071* (2010.01)
*C12N 5/00* (2006.01)
(Continued)

(52) U.S. Cl.
CPC . *C12N 5/069* (2013.01); *A61F 2/06* (2013.01); *A61L 27/507* (2013.01); *C12N 5/0068* (2013.01); *C12N 5/0691* (2013.01); *C12N 2535/10* (2013.01)

(58) Field of Classification Search
None
See application file for complete search history.

(56) References Cited

U.S. PATENT DOCUMENTS 5,202,227 A 4/1993 Matsuda et al.
5,470,739 A 11/1995 Akaike et al.
(Continued)

FOREIGN PATENT DOCUMENTS

JP 2-084174 A 3/1990
JP 8-009960 A 1/1996
(Continued)

OTHER PUBLICATIONS

Nasim Akhtar, et al; "The sponge/Matrigel angiogenesis assay", Angiogenesis, vol. 5, Issues 1-2, pp. 75-80; Mar. 2002.
(Continued)

*Primary Examiner* — Allison Fox
(74) *Attorney, Agent, or Firm* — Ladas & Parry LLP

(57) ABSTRACT

An artificial tissue capable of carrying necessary nutrients for maintaining activities of cells and tissues, and method of manufacturing artificial blood vessel. A plurality of forms of blood vessels are extracted from an image of living tissue and made into blood vessel form image. Each of the blood vessel forms of the blood vessel form image is adjusted and a blood vessel formation pattern is formed. A blood vessel cell culturing pattern of forming is formed, in a cell culturing layer. The blood vessel cell culturing pattern includes: a cell adhesion portion having adhesive properties with blood vessel cell and formed to the blood vessel formation pattern; and a cell adhesion-inhibiting portion having cell adhesion-inhibiting properties for inhibiting adhesion with a blood vessel cell and formed in an area other than the cell adhesion portion. A blood vessel cell is adhered to the cell adhesion portion, and cultured into tissue.

16 Claims, 3 Drawing Sheets

(51) Int. Cl.
*A61F 2/06* (2013.01)
*A61L 27/50* (2006.01)

(56) References Cited

U.S. PATENT DOCUMENTS

| 7,687,251 B2 | 3/2010 | Hattori et al. |
| 2002/0111546 A1 | 8/2002 | Cook et al. |

FOREIGN PATENT DOCUMENTS

| JP | 10-243924 A | 9/1998 |
| JP | 2003-527615 A | 9/2003 |
| JP | 2005-143382 A | 6/2005 |
| JP | 2005-160441 A | 6/2005 |
| WO | 96/15223 A1 | 5/1996 |
| WO | 00/60356 A1 | 10/2000 |
| WO | 01/70389 A2 | 9/2001 |

OTHER PUBLICATIONS

Robert Auerbach, et al; "Angiogenesis Assays: A Critical Overview", Clinical Chemistry, vol. 49, Issue 1, pp. 32-40; Jan. 2003.

Maria Grazia Cattaneo, et al; "Alprostdil suppresses angiogenesis in vitro and in vivo in the murine Matrigel plug assay", *British Journal of Pharmacology*, vol. 138, pp. 377-385; Jan. 2003.

Subhasis Chaudhuri, et al; "Detection of Blood Vessels in Retinal Images Using Two-Dimensional Matched Filters", IEEE Transactions on Medical Imaging, vol. 8, No. 3, XP-002674070, Sep. 1989, pp. 263-269.

Albert Folch, et al: "Microengineering of Cellular Interactions", Annual review of biomedical engineering, vol. 2, Issue 2, pp. 227-256; Aug. 2000.

General Matrigel Angiogenesis Assay, Apr. 21, 2004 (from http://www.mcdb.ucla.edu/Research/Arispe/Protocols/Matrigel.pdf.

Donald E. Ingber, et al; "Mechanochemical Switching between Growth and Differentiation during Fibroblast Growth Factor-stimulated Angiogenesis In Vitro: Role of Extracellular Matrix", The Journal of Cell Biology, vol. 9, Jul. 1989; pp. 317-330.

Naoto Kolke, et al; "Creation of long-lasting blood vessels", Nature, vol. 428, Mar. 11, 2004, pp. 138-139.

Wakana Kubo, et al; "Mechanisms and Resolution of Photocatalytic Lighography", J. Phys. Chem. B. vol. 108, Issue 9, pp. 3005-3009; Publication Date (Web): Feb. 5, 2004.

Nicolas L'Heureux, et al; "A completely biological tissue-engineered human blood vessel", FASEB J. Jan. 1998; vol. 12, Issue 1, pp. 47-56.

Takehisa Matsuda, et al; "Two-dimensional Cell Manipulation Technology An Artificial Neural Circuit Based on Surface Microphotoprocessing", ASAIO Journal, vol. 39(3), Jul.-Sep. 1992, pp. M243-M247.

B.J. Spargo, et al; "Spatially controlled adhesion, spreading, and differentiation of endothelial cells on self-assembled molecular monolayers", Proc. Natl Acad Sci U.S.A., Nov. 8, 1994, vol. 91(23): pp. 11070-11074.

Crispin B. Weinberg, et al; "A Blood Vessel Model Contructed form Collagen and Cultured Vascular Cells", Science, vol. 231, pp. 397-400; Jan. 24, 1986.

International Search Report mailed Aug. 23, 2005; PCT/JP2005/009917.

Supplementary European Search Reprot: dated Feb. 5, 2012; Appln. No. 05745973.7-1219 / 1759720 PCT/JP2005009917.

USPTO RR mailed May 15, 2009 in connection with U.S. Appl. No. 11/597,975.

USPTO NFOA mailed Jul. 8, 2009 in connection with U.S. Appl. No. 11/597,975.

USPTO FOA mailed Apr. 14, 2010 in connection with U.S. Appl. No. 11/597,975.

USPTO NFOA dated Mar. 21, 2012 in connection with U.S. Appl. No. 11/597,975.

USPTO NOA mailed Oct. 4, 2012 in connection with U.S. Appl. No. 11/597,975.

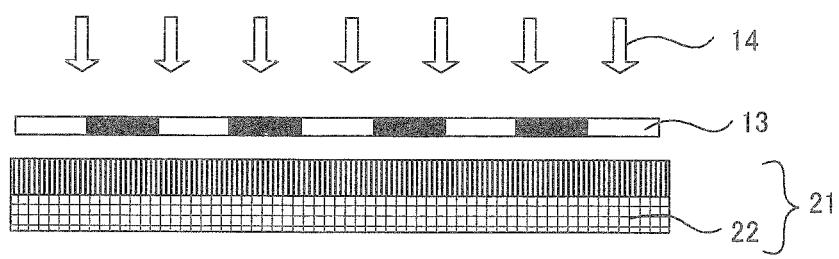
FIG. 4A
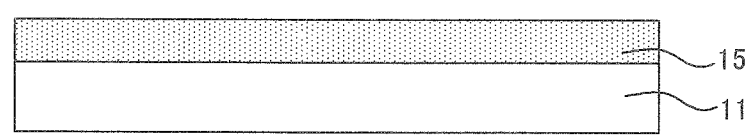
FIG. 4B
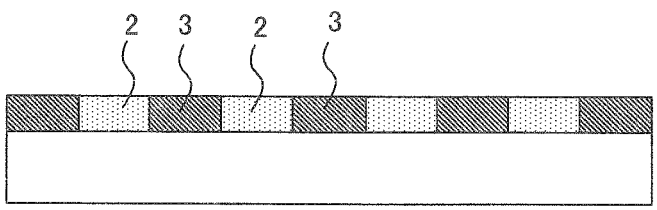
FIG. 5
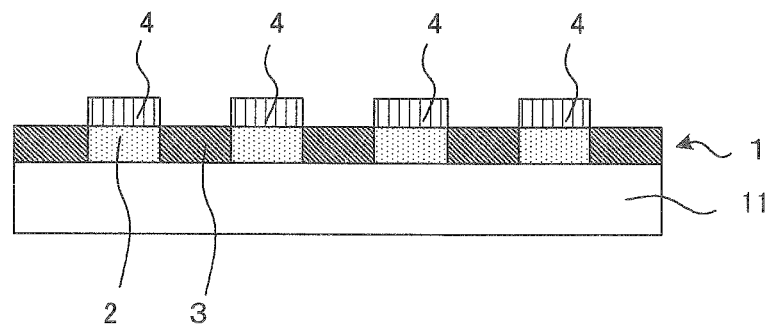

US 9,359,594 B2

ARTIFICIAL BLOOD VESSEL AND METHOD OF MANUFACTURING THEREOF

TECHNICAL FIELD

The present invention relates to an artificial blood vessel used in the field of the regenerative medicine or the like.

BACKGROUND ART

At present, cell cultures of various animals and plants are performed, and also new cell culture methods are in development. The technologies of the cell culture are utilized, such as to elucidate the biochemical phenomena and natures of cells and to produce useful substances. Furthermore, with cultured cells, an attempt to investigate the physiological activity and toxicity of artificially synthesized medical is underway. Moreover, in the field of the medicine and others, artificial production of tissues and organs has been attempted by re-organizing such as cells, proteins, glucides, or lipids of living bodies by the technique of the cell engineering, or the like.

Here, since the common animal cells perish without supply of the nutrients, or the like, in the case of using cultured cells as, for example, the artificial tissues, it is necessary to provide the capillary blood vessels in the artificial tissues and the blood for passing through therein for supplying such as the oxygen or nutrients, and carrying out the metabolic decomposition products. Moreover, disorders, in which an infarct in micro blood vessels within the living body occurs, and the supply of oxygen and nutrients or the transfer of metabolic decomposition products are not sufficiently performed exist.

To respond to such problems, conventionally, for example, artificial formation of the capillary blood vessels has been attempted by the techniques of the Non-Patent Documents 1 to 3, however, in either case, only the vessel-like tissues (capillaries) are formed in disorder so that it has been difficult to form capillary blood vessels capable of providing a necessary amount of the blood to a desired position for maintaining the function of the artificial tissues or infarct site treatment of micro blood vessels. Moreover, as described in Non-Patent Document 4 or 5, a forming method of blood vessels by utilizing an artificial material has been studied, however, it is difficult to form narrow blood vessels and the artificial blood vessels which can be utilized for infarct site treatment of micro blood vessels and the construction of an artificial tissue could not be formed.

On the other hand, the present inventors have proposed a method of culturing cells in a pattern by changing the surface of a layer having cell adhesive properties or cell adhesion-inhibiting properties by the function of a photocatalyst accompanied by the irradiation with energy for forming a pattern comprising a cell adhesion portion and a cell adhesion-inhibiting portion and highly accurately adhering the cells only to the cell adhesion portion. According to the patterning method, the cells are stimulated at the boundary of the cell adhesion portion and the cell adhesion-inhibiting portion so that the cells adhered in a pattern can be aligned or the morphological change to the stretching state can be promoted strongly as a result. Using the present method, it became possible that by culturing vascular endothelial cells in a pattern form and further by making an anchorage material for deriving the vascular endothelial cells into a blood vessel tissue in contact with the endothelial cells and transcribing the cells, a narrow blood vessel tissue along the desired pattern is formed. However, the technology for forming these blood vessels in a form suitable for the infarction site treatment of the micro blood vessels and the construction of the above-described artificial tissue has not yet been invented.

[Non-Patent Documents 1] D. E. Ingber, et al., The Journal of Cell Biology (1989) p. 317-
[Non-Patent Documents 2] B. J. Spargo, et al., Proceedings of the National Academy of Sciences of the United States of America (1994) p. 11070-
[Non-Patent Documents 3] R. Auerbach et al., Clinical Chemistry (2003) p. 32-
[Non-Patent Documents 4] C. B. Weinberg, et al., Science (1986) p. 397-
[Non-Patent Documents 5] N. L'. Heureux, et al., The FASEB Journal (1998) vol. 12 p. 47-

DISCLOSURE OF THE INVENTION

Problem to be Solved by the Invention

From the descriptions set forth above, it is necessarily required that oxygen and nutrients necessary for maintaining the functions are efficiently supplied and a metabolic decomposition product is sent out for the purpose of treating the infarct site of micro blood vessels and constructing an artificial tissue and organ. Accordingly, it has been desired that a method of manufacturing an artificial blood vessel formed in a form suitable for the infarct site treatment of micro blood vessels and an artificial tissue constructed outside of the living body is provided.

Means for Solving the Problem

The present invention provides a method of manufacturing an artificial blood vessel, characterized in that the method comprises: a process for extracting a blood vessel form image of extracting a plurality of forms of blood vessels from an image of a living tissue and making it into a blood vessel form image; a process for adjusting a blood vessel forming pattern of adjusting each of the blood vessel forms of the blood vessel form image and forming a blood vessel formation pattern; a process for forming a blood vessel cell culturing pattern of forming, in a cell culturing layer, a blood vessel cell culturing pattern comprising: a cell adhesion portion having adhesive properties with a blood vessel cell and formed to the blood vessel formation pattern, and a cell adhesion-inhibiting portion having cell adhesion-inhibiting properties for inhibiting adhesion with a blood vessel cell and formed in an area other than the cell adhesion portion; and a process for culturing a blood vessel cell of adhering a blood vessel cell to the cell adhesion portion, culturing and made into a tissue.

As a form of artificial blood vessels suitable for the infarction site treatment of micro blood vessels and an artificial tissue constructed outside of the living body, there is a form mocking the structure of blood vessels in a tissue of the living body. In a tissue of the living body, oxygen, nutrients and metabolic decomposition products which are necessary for cells in the tissue to activate are carried via blood.

According to the present invention, since in a process for forming the above-described blood vessel cell culturing pattern, the above described cell adhesion portion which has been adjusted so that the blood vessel cell can form blood vessels in a blood vessel pattern form of the living body tissue is formed, it becomes possible to form artificial blood vessels in a pattern form similar to the blood vessels of the living body tissue in a process for culturing blood vessel cell. Owing to this, it is capable of, for example, supplying nutrients from the blood vessels to cells in a tissue similar to the case of the tissue of the living body by disposing artificial blood vessels manufactured according to the present invention at the infarction site of micro blood vessels or in the artificial tissue. Moreover, in the present invention, a blood vessel form image obtained from the image of the living body tissue is adjusted in the above-described process for adjusting a blood vessel forming pattern, it becomes possible that the blood vessels are efficiently formed in a pattern form to be targeted by utilizing the above-described process for forming a blood vessel cell culturing pattern and the process for culturing a blood vessel cell.

In the above-described invention, the above-described process for forming a blood vessel cell culturing pattern can be made into a process for forming blood vessel cell culturing pattern by irradiating the energy to the above-described cell culturing layer which can form the above-described cell adhesion portion and the above-described cell adhesion-inhibiting portion by action of a photocatalyst accompanying with the energy irradiation. In this case, it has an advantage that at the time when the above-described blood vessel cell culturing pattern is formed, blood vessel cell culturing pattern can be formed easily and at a finely processed level without utilizing complex processes such as a process for utilizing chemicals which have an adverse influence upon the cell.

According to the present invention, a method of manufacturing an artificial tissue characterized in that it utilizes the artificial blood vessel manufactured by the above-described blood vessel manufacturing method is provided. According to the present invention, since artificial blood vessels manufactured by the above-described manufacturing method is used, nutrients can be supplied to cells in the manufactured artificial tissue similar to the tissue of the living body and so on, and the artificial tissue can be used for a variety of uses.

The present invention further provides a photomask, characterized in that the photomask has a blood vessel pattern comprising a two-dimensional pattern constituted with a line width in which a vascular endothelial cell is in a tubular form.

According to the present invention, since a photomask has a blood vessel pattern comprising a two-dimensional pattern constituted by the line width in which the vascular endothelial cell is in a tubular form, by utilizing this photomask, for example, a cell adhesion portion having the adhesive properties with a cell is formed in a blood vessel form in a living body tissue by patterning the cell culturing layer, and the vascular endothelial cells can be cultured on the cell adhesion portion and made these into a tubular form. Owing to this, the blood vessels can be formed into a targeted pattern, and for example, artificial blood vessels having a pattern similar to the blood vessels of the living body tissue can be formed.

The present invention further provides an artificial blood vessel, characterized in that the artificial blood vessel has a blood vessel pattern formed by a two-dimensional pattern constituted with a line width in which a vascular endothelial cell is in a tubular form.

Since artificial blood vessels of the present invention have a blood vessel pattern formed by utilizing a two-dimensional pattern constituted by a line width in which a vascular endothelial cell is to be a tubular form, for example, it can be made artificial blood vessels which can be applied for a variety of uses such as for a living tissue grafting, or for artificial tissue.

The present invention further provides an artificial tissue, characterized by comprising the artificial blood vessel.

Since an artificial tissue of the present invention has artificial blood vessels having a form of blood vessels of a living tissue, it can supply nutrients to the cells similar to the living tissue cell so that it can be used for a variety of uses.

Moreover, the present invention provides a blood vessel cell culturing pattern base material comprising: a base material; a cell culturing layer formed on the base material and having a pattern comprising a cell adhesion portion having adhesive properties with a blood vessel cell and a cell adhesion-inhibiting portion for inhibiting adhesion with a blood vessel cell; and a blood vessel cell adhered to the cell adhesion portion, characterized in that the cell adhesion portion is formed in a blood vessel pattern comprising a two-dimensional pattern constituted with a line width in which a vascular endothelial cell is in a tubular form.

According to a blood vessel cell culturing pattern base material of the present invention, these can be cultured in a finely processed pattern form that the blood vessel cells are targeted on the above-described cell adhesion portion.

The present invention further provides a vascular endothelial cell pattern base material comprising a base material and a vascular endothelial cell provided on the base material in such a way that the cell can be peeled off, characterized in that the vascular endothelial cell is formed with a line width in which the endothelial cell is in a tubular form in a pattern that a blood vessel network is represented in two-dimension.

In the vascular endothelial cell pattern base material of the present invention, since a vascular endothelial cell formed in a predetermined pattern has been provided in a state where the vascular endothelial cell can be peeled off, it can be used for a variety of uses, for example, for artificial tissue by peeling off the vascular endothelial cell.

Effect of the Invention

According to the present invention, it is possible that, for example, nutrients can be supplied to a cell in a tissue similar to a living tissue, the present invention exerts the effect that artificial blood vessels capable of being used for a variety of uses can be efficiently formed in a pattern in which artificial blood vessels are targeted.

BRIEF DESCRIPTION OF THE DRAWINGS

FIGS. 4A and 4B are illustrations for explaining one example of a process for forming a blood vessel cell culturing pattern in a manufacturing method of an artificial blood vessel of the present invention; and FIG. 5 shows a schematically sectioned view for illustrating one example of a blood vessel cell culturing pattern base material of the present invention.

DESCRIPTION OF REFERENCE NUMERALS

1 . . . cell culturing layer,
2 . . . cell adhesion portion, and
3 . . . cell adhesion-inhibiting portion.

BEST MODE FOR CARRYING OUT THE INVENTION

The present invention relates to an artificial blood vessel used such as in the field of regenerative medicine and a manufacturing method thereof, an artificial tissue in which the artificial blood vessels have been used and the manufacturing method thereof, a photomask which is used at time when these are manufactured, and a blood vessel cell culturing pattern base material forming the artificial blood vessel. Hereinafter, these will be explained in detail, respectively.

A. A Method of Manufacturing an Artificial Blood Vessel

First, the method of manufacturing an artificial blood vessel will be explained. The method of manufacturing an artificial blood vessel of the present invention is characterized in that the method comprises: a process for extracting a blood vessel form image of extracting a plurality of forms of blood vessels from an image of a living tissue and making it into a blood vessel form image; a process for adjusting a blood vessel forming pattern of adjusting each of the blood vessel forms of the blood vessel form image and forming a blood vessel formation pattern; a process for forming a blood vessel cell culturing pattern of forming, in a cell culturing layer, a blood vessel cell culturing pattern comprising: a cell adhesion portion having adhesive properties with a blood vessel cell and formed to the blood vessel formation pattern, and a cell adhesion-inhibiting portion having cell adhesion-inhibiting properties for inhibiting adhesion with a blood vessel cell and formed in an area other than the cell adhesion portion; and a process for culturing a blood vessel cell of adhering a blood vessel cell to the cell adhesion portion, culturing and made into a tissue.

Figure 1A:
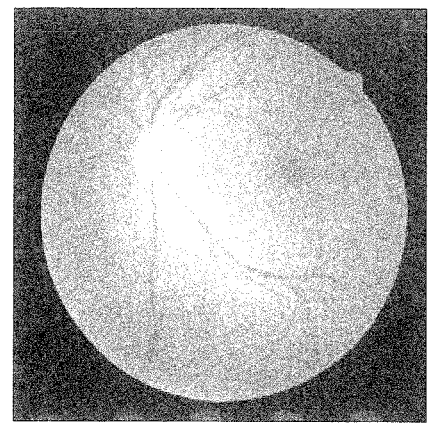
FIGS. 1A to 1C are each a photograph and illustrations for explaining one example of a method of manufacturing an artificial blood vessel of the present invention.
Figure 1B:
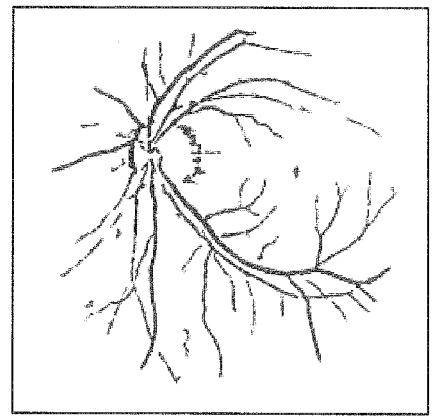
Figure 1C:
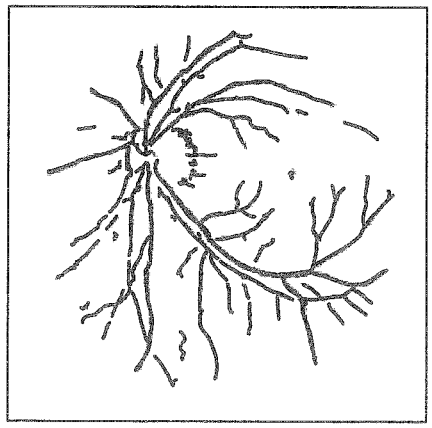
Figure 2A:
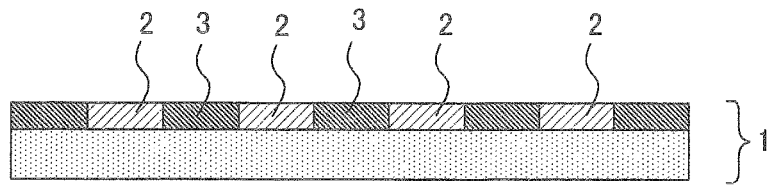
FIGS. 2A and 2B are illustrations for explaining one example of a method of manufacturing an artificial blood vessel of the present invention.
Figure 2B:
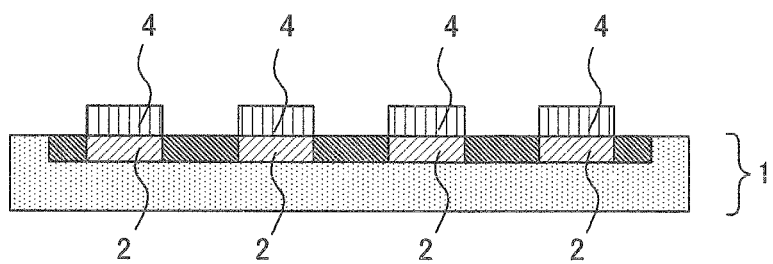

A method of manufacturing an artificial blood vessel of the present invention has, for example, as shown in FIGS. 1A to 1C, a process for extracting a blood vessel form image in which a form of blood vessels is extracted from an image of a living tissue (FIG. 1A) and made it into the blood vessel form image (FIG. 1B); a process for adjusting a blood vessel forming pattern in which the respective blood vessel forms of the blood vessel form image (FIG. 1B) and made it into the blood vessel forming pattern (FIG. 1C); for example as shown in FIGS. 2A and 2B, a process for forming a blood vessel cell culturing pattern (FIG. 2A) for forming a blood vessel culturing pattern on the cell culturing layer 1 comprising a cell adhesion portion 2 which has been formed in the above-described blood vessel forming pattern, and a cell adhesion-inhibiting portion 3 which is the area other than the cell adhesion portion 2; and a process for culturing a blood vessel cell (FIG. 2B) in which a blood vessel cell 4 is adhered to the cell adhesion portion 2 of the blood vessel cell culturing pattern and cultured and made into a tissue.

A living tissue as used herein refers to a tissue formed by blood vessels and the other cells and the like existing in the living body and also means various kinds of organs such as kidney and liver, ocular fundus, and skin.

According to the present invention, in the process for forming blood vessel cell culturing pattern, since a cell adhesion portion having the cell adhesive properties with a blood vessel cell is formed, on the cell culturing layer, in a form of a blood vessel forming pattern which is a pattern similar to blood vessels in the living tissue, in the process for culturing a blood vessel cell, the blood vessel cell can be adhered only to the cell adhesion portion and cultured, and not adhered to the cell adhesion-inhibiting portion. Owing to this, it becomes possible that artificial blood vessels are formed in the pattern similar to the blood vessels of the living tissue. Accordingly, nutrients can be supplied similarly to the living tissue, for example, by disposing the artificial blood vessel in the tissue cell such as at the infarct site of micro blood vessels, or in an artificial tissue.

Moreover, in the present invention, since the blood vessel form image derived from the image of the living tissue obtained in the process for adjusting a blood vessel forming pattern is adjusted into a form in which artificial blood vessels are easily formed and so on in the blood vessel cell culturing pattern forming process and the blood vessel cell culturing process, it becomes possible that artificial blood vessels are efficiently formed into a targeted pattern, and it is also preferable from the viewpoint of such as manufacturing efficiency.

Hereinafter, the respective processes of a method of manufacturing an artificial blood vessel of the present invention will be explained in detail.

1. Blood Vessel Forming Image Extracting Process

First, the blood vessel forming image extracting process of the present invention will be explained below. The blood vessel forming image extracting process of the present invention is a process of extracting a form of blood vessels from the image of the living tissue to make a blood vessel form image. The method is not particularly limited as long as it is a method capable of obtaining an image extracting the form of blood vessels from the image of the living tissue.

As an image of the living tissue used in the present process, it is not particularly limited as long as the image is an image that the tissue within the living body has been imaged and that can specify the form of the blood vessels. As the image, for example, an image which has been three-dimensionally shot may be the one, however it is particularly preferable that it is an image which has been two-dimensionally shot. This is because the adjustment in the process for adjusting a blood vessel forming pattern described later becomes easy by utilizing an image which has been two-dimensionally shot. As a method of shooting the image, for example, a method of directly observing blood vessels in the living tissue as shown in blood vessels of skin or ocular fundus, a method of directly shooting the cross-section of the living tissue, a method of imaging it by injecting a contrast and opaque media into the blood vessels of the targeted living tissue and irradiating nuclear radiation, or a method of using MRI (magnetic resonance imaging) can be used.

In the present process, from an image of the living tissue described above, only the image of blood vessels is extracted. Most of the above-described method of acquiring an image of blood vessels contains noise or the like derived from the tissue other than blood vessels. Accordingly, as a method of extracting only the image of the blood vessels, in order to remove the contour of the living tissue and the noise, it is general that a binary treatment and a treatment of expanding and retracting an image are performed with respect to the obtained image to take out an image of blood vessels.

2. Blood Vessel Formation Pattern Adjusting Process

Next, the blood vessel formation pattern adjusting process in the present invention will be explained below. The blood vessel formation pattern adjusting process in the present invention is a process in which the forms of the respective blood vessels of the blood vessel form images extracted by the process for extracting a blood vessel form image is adjusted to form a blood vessel forming pattern. In the present process, the form of the artificial blood vessels formed by the process for forming a blood vessel cell culturing pattern and the process for culturing a blood vessel cell described later is to be determined by adjusting the form of the blood vessels of a blood vessel form image.

As an adjustment of a form of the respective blood vessels in the present process, for example, the adjustment of the line width of the blood vessels in the above-described blood vessel form image can be listed. Since it can be made that artificial blood vessels can be efficiently formed by adjusting the width of the respective blood vessels of the blood vessel form image to a width suitable for forming artificial blood vessels in the blood vessel cell culturing pattern forming process and the blood vessel forming pattern adjusting process; that is the line width in which a vascular endothelial cell is in a tubular form. As the line width of blood vessels of a blood vessel cell culturing pattern formed in the process for forming a blood vessel cell culturing pattern described later using the above-described blood vessel forming pattern, it is preferable to be usually in the range from 20 µm to 100 µm, more preferable to be in the range from 40 µm to 80 µm, and it is particularly preferable to be in the range from 50 µm to 70 µm. In the case where the diameter of the blood vessel in the blood vessel form image is smaller than the above-described range, it is desired that the blood vessel cell culturing pattern is changed into the suitable diameter for forming the blood vessels. It should be noted that in the case where the diameter of the blood vessels in the blood vessel form image is larger than the above-described range and so on, for example, it might be made into a pattern of several pieces of blood vessels branched in the above-described range to secure the necessary flow of the blood. At this time, usually, the line width of the respective blood vessels is formed so as to be the same line width. And further, in the case where the diameter of the blood vessel in the blood vessel form image is larger than the above-described range, an auxiliary pattern may be formed in the blood vessel pattern. The auxiliary pattern is a fine pattern formed within the blood vessel pattern, and the area where this auxiliary pattern has been formed is made into a cell adhesion-inhibiting portion for inhibiting the adhesion with a blood vessel cell in a blood vessel cell culturing pattern formed by the process for forming a blood vessel cell culturing pattern described later. It should be noted that, when the blood vessel cells are adhered to the blood vessel cell adhesion portion formed in pattern, the auxiliary pattern is formed in such a degree that the cell adhesion-inhibiting portion corresponding to the auxiliary pattern becomes a fine pattern which does not inhibit the binding of the blood vessel cells within the cell adhesion portion; specifically, in such a degree that the blood vessel cells can be bound with one another even on the cell adhesion-inhibiting portion corresponding to the auxiliary pattern.

Generally, in the case where a tissue is formed by adhering a blood vessel cell to the cell adhesion portion corresponding to the blood vessel pattern and culturing the cell, the blood vessel cells are gradually aligned from the outside to the inside of the cell adhesion portion. Moreover, at the time when the tissue is formed, it is necessary to align the blood vessel cells after the forms of the respective blood vessel cell are changed, and also concerning with the changing of the form of the blood vessel cells, it is gradually performed from the end portion to the central portion of the cell adhesion portion. Therefore, in the case where the width of the cell adhesion portion is large, the alignment property of the blood vessel cells is poor at the central portion of the cell adhesion portion, and there are cases where the tissue is not formed, where the blood vessel cells are adhered to the central portion of the cell adhesion portion and the like. Accordingly, since it becomes possible that the blood vessel cells are aligned from the end portion of the cell adhesion-inhibiting portion and the form can be changed by forming the cell adhesion-inhibiting portion corresponding to the auxiliary pattern, the blood vessel cells can be cultured in a targeted pattern form without generating the deletion and the failure in the form change. Moreover, since the cell adhesion-inhibiting portion corresponding to the auxiliary pattern is formed so that the adhesion between the blood vessel cells adjoining to one another sandwiching the cell adhesion-inhibiting portion is not inhibited, as the width of the blood vessel cells which are to be finally cultured, it can be the width similar to the width corresponding to the pattern of the above-described blood vessels.

Here, it is preferable that the auxiliary pattern is formed in a line form within the pattern of the blood vessels. Moreover, the form of the line is not particularly limited and it can be made, for example, into a linear form, curve form, dotted form, and broken line form. It is preferable that the line width of the auxiliary pattern is formed such that the width of the corresponding cell adhesion-inhibiting portion becomes in the range from 0.5 µm to 10 µm, particularly in the range from 1 µm to 5 µm at the time when the blood vessel cell culturing pattern was formed. In the case where the width is wider than the above-described range, it is not preferable since it becomes difficult for blood vessel cells adjoining to one another sandwiching the cell adhesion-inhibiting portion corresponding to the auxiliary pattern to interact on the cell adhesion-inhibiting portion.

Moreover, the auxiliary pattern may be formed to have a convexvoncavo pattern such as a zig-zag form within the surface. At this time, it may be formed such that the average value of the distance from the end of the convex portion to the end of the concave portion of the convexvoncavo pattern becomes a distance in which the blood vessel cells are lined-up in a direction similar to the line direction of the cell adhesion portion at the time when the blood vessel cells were adhered to the cell adhesion portion corresponding to the pattern of the above-described blood vessels. It is preferable that it is formed such that the convexvoncavo is in the range form 0.5 µm to 30 µm particularly at the time when the blood vessel cell culturing pattern described later was formed. It should be noted that as for the measurement of the average distance from the end of the concave portion to the end of the convex portion of the convexvoncavo, the distance from the bottom portion to the apex portion of the respective convex-voncavo in the range of the length of 200 µm of the end portion of the cell adhesion-inhibiting portion corresponding to the auxiliary pattern is measured, and it is made a value that the average was calculated.

Moreover, in the present process, it is preferable that the adjustment for amending the unclear portion and minute portion is performed. This is because it becomes difficult to form the blood vessels in a targeted pattern form in the process for forming a blood vessel cell culturing pattern and the process for culturing blood vessel cells described later in the case where the blood vessel cell culturing pattern has the unclear portion and the like. Moreover, at this time, it may be adjusted by removing the unnecessary blood vessels. This is because in the case where the form of the blood vessels not existing on the same plane is in the blood vessel form image, for example, in the case where the blood vessel form image is an image three-dimensionally shot and so on, it is preferable to remove this portion.

Moreover, since the blood vessel form image which exists in three-dimension is expressed in two-dimension, although the interval between the blood vessels is originally wide, there are a case where the interval is expressed as it is narrow, or a case where the angle of the branch is expressed to be more acute angle m than the original angle. In the above-described cases, in the present process, the adjustment that widens the interval between the blood vessels and the adjustment to make the angle of the branch obtuse angle, and the like can be performed. Furthermore, in order to express the three-dimensional blood vessel network in two-dimension where the blood vessels do not cross, the adjustment for exchanging the end portion of one of the crossed blood vessels can be performed. Moreover, further, in the case where the blood flow of the blood vessels can be made better without damaging the function that the blood vessels carries out and so on, the form of the blood vessels may be adjusted, for example, by making the blood vessels formed in a curve form in the living tissue linear form.

Moreover, at the time when the blood vessels manufactured by the present invention are used for the living body and artificial tissue and so on, since it is naturally a state where the blood is flown in the blood vessels and these are used, the adjustment maybe formed so that it becomes a pattern such that it has the blood vessels not existing in the blood vessel form image for the purpose of communicating the blood vessels in the living body and the respective blood vessels. As for the blood vessels described above, the diameter and the location where it is formed are appropriately adjusted by such as the direction where the blood flows or the pressure applied to the blood vessels.

The adjustment of the respective blood vessels as described above can be performed by image treating a blood vessel form image and so on.

3. Blood Vessel Cell Culturing Pattern Forming Process

Next, the blood vessel cell culturing pattern forming process in the present invention will be explained below. The blood vessel cell culturing pattern forming process in the present invention is a process of forming, in the cell culturing layer, a blood vessel cell culturing pattern comprising: the cell adhesion portion having adhesive properties with a blood vessel cell and formed to a form of the above-described blood vessel forming pattern; and the cell adhesion-inhibiting portion having the cell adhesion-inhibiting properties for inhibiting the adhesion with the blood vessel cells and formed in the area other than the cell adhesion portion. It should be noted that at the time when the blood vessel cell culturing pattern is formed using a blood vessel forming pattern, the size of the above-described cell culture portion may be made the size same with the blood vessel forming pattern. Alternatively, the cell adhesion portion may be formed such that the size of the blood vessel forming pattern is expanded or retracted. Owing to this, because it becomes possible that the blood vessel cell culturing pattern having a variety of sizes is formed by means of the one blood vessel forming pattern.

In the present process, by forming the blood vessel cell culturing pattern, in the cell culturing layer, comprising the cell adhesion portion and the cell adhesion-inhibiting portion, it becomes possible that the blood vessel cells are easily cultured in the blood vessel forming pattern by the process for culturing blood vessel cells described later. Here, to have the adhesive properties with blood vessel cells means that it excellently adheres to the blood vessel cells; and in the case where the adhesive properties with the blood vessel cells is different according to the kinds of the blood vessel cells and so on, it means that it excellently adheres to the targeted blood vessel cells. Moreover, to have the cell adhesion-inhibiting properties with the blood vessel cells means that it has the nature for inhibiting the adhesion of the blood vessel cells; and in the case where the cell adhesion-inhibiting properties with the blood vessel cells are different according to the kinds of the blood vessel cells and so on, it means that the adhesion with the targeted blood vessel cells is inhibited.

As for cell culturing layer used in the present process, if it is a layer which is capable of forming a blood vessel cell culturing pattern comprising the cell adhesion portion and the cell adhesion-inhibiting portion in the cell culturing layer, it is not particularly limited. It may also be a layer having the cell adhesive properties or a layer having the cell adhesion-inhibiting properties. Moreover, in the present invention, if it is necessary, the cell culturing layer may be formed on the base material.

In the present process, if it is a method capable of forming a blood vessel cell culturing pattern having the cell adhesion portion and the cell adhesion-inhibiting portion, a forming method, is not particularly limited. For example, it can be made a method in which a mask having the light shielding portion in a pattern form of the blood vessel formation pattern and a material having the cell adhesion-inhibiting properties is coated in a pattern form on the cell culturing layer having the cell adhesive properties by a printing method and the like; or a method in which a layer having the cell adhesion-inhibiting properties is formed on the cell culturing layer having the cell adhesive properties and patterned in a pattern form of the cell adhesion-inhibiting portion by a photolithography method or the like. Moreover, it may be a method in which a mask having the opening portion in a pattern form of the blood vessel formation pattern is formed and a material having the cell adhesive properties is coated in a pattern form on the cell culturing layer having the cell adhesion-inhibiting properties to form the cell adhesion portion; or a forming method of the cell adhesion portion by patterning with a photolithography method similar to the description set forth above.

Here, in the present invention, it is preferable that the above-described cell culturing pattern is formed by irradiating the energy on the cell culturing layer in which the cell adhesion portion and the above-described cell adhesion-inhibiting portion can be formed by the action of the photocatalyst accompanying with the energy irradiation. In this case, the formation of the cell adhesion portion and the cell adhesion-inhibiting portion can be easily performed without utilizing chemicals or the like which adversely affect the blood vessel cells and without performing the complex process. It should be noted that as a forming method of the blood vessel cell culturing pattern by the action of the photocatalyst accompanying with the energy irradiation, the following six embodiments are listed. Hereinafter, each of embodiments will be explained.

(1) First Embodiment

First, as a first embodiment, the cell culturing layer is a photocatalyst-containing cell adhesion layer comprising at least photocatalyst, the adhesive properties with cells and a blood vessel cell adhesive material which is decomposed or denatured by the action of a photocatalyst accompanying with the energy irradiation; and it is a case where for example, the cell adhesion-inhibiting portion is formed by decomposing or denaturing the blood vessel cell adhesive material by irradiating energy using such as a photomask having the light shielding portion in a pattern form of the blood vessel formation pattern on the photocatalyst-containing cell adhesion layer.

According to the present embodiment, since the photocatalyst-containing cell adhesion layer contains a photocatalyst and the blood vessel cell adhesive material, the area where the energy has been irradiated can be made the cell adhesion-inhibiting portion which is not adhered to the blood vessel cells by decomposing or denaturing the blood vessel cell adhesive material. On the other hand, since the area where the energy is not irradiated can be made the cell adhesion portion which is excellent in the adhesive properties with the blood vessel cells since the blood vessel cell adhesive material remains.

Moreover, according to the present embodiment, in the process for culturing blood vessel cell described later, the blood vessel cells adhered to the cell adhesion-inhibiting portion can be removed by the action of the photocatalyst by irradiating energy to the cell adhesion-inhibiting portion at the time when the blood vessel cell is adhered to the cell adhesion portion, cultured and made into a tissue. Owing to this, it has an advantage that the blood vessels can be formed in a further finely processed pattern.

Hereinafter, a forming method of a photocatalyst-containing cell adhesion layer and a cell adhesion-inhibiting portion which are used in the present embodiment will be explained below.

a. Photocatalyst-Containing Cell Adhesion Layer

First, a photocatalyst-containing cell adhesion layer used in the present embodiment will be explained below. A photocatalyst-containing cell adhesion layer used in the present embodiment at least contains a photocatalyst and the above-described blood vessel cell adhesive material, and the photocatalyst-containing layer is a layer in which the blood vessel cell adhesive material is decomposed or denatured by the action of the photocatalyst accompanying with the energy irradiation to lower the adhesive properties with the cell.

The formation of the photocatalyst-containing cell adhesion layer described above can be performed, for example, by coating, on a base material, a coating solution for forming a photocatalyst-containing cell adhesion layer containing: a blood vessel cell adhesive material which is decomposed and denatured by the action of the photocatalyst accompanying with the energy irradiation, and the photocatalyst. The coating of the coating solution for formation of the photocatalyst-containing cell adhesion layer can be performed using a general method of coating such as a spin coat method, a spray coat method, a dip coat method, a roll coat method, and a bead coat method.

At this time, as the thickness of a film of the photocatalyst-containing cell adhesion layer, usually, it is in the range from about 0.01 μm to about 1.0 μm, and it is preferably in the range from about 0.1 μm to about 0.3 μm.

Hereinafter, the respective materials used in the photocatalyst-containing cell adhesion layer used in the present embodiment will be explained below.

(i) Blood Vessel Cell Adhesive Material

First, a blood vessel cell adhesive material contained in a photocatalyst-containing cell adhesion layer of the present embodiment will be explained below. As for a blood vessel cell adhesive material contained in a photocatalyst-containing cell adhesion layer of the present embodiment, the kind or the like is not particularly limited as long as it has the adhesive properties with blood vessel cells and it is decomposed or denatured by the action of the photocatalyst accompanying with the energy irradiation.

The blood vessel cell adhesive material used in the present embodiment has the adhesive properties with the blood vessels, and such as those which loses the adhesive properties with the blood vessel cell or those being changed to have the cell adhesion-inhibiting properties for inhibiting the adhesion with the blood vessel cell by being decomposed or denatured by the action of the photocatalyst accompanying with the energy irradiation.

As such materials having the adhesive properties to a blood vessel cell, there are two kinds. One is being materials having the adhesive properties to a blood vessel cell owing to physicochemical characteristics and the other being materials having the adhesive properties to a blood vessel cell owing to biochemical characteristics.

As physicochemical factors that determine the adhesive properties to a blood vessel cell of the materials having the adhesive properties to a blood vessel cell owing to the physicochemical characteristics, the surface free energy, the electrostatic interaction and the like can be cited. For instance, when the adhesive properties to a blood vessel cell is determined by the surface free energy of the material, the adhesive properties between the blood vessel cell and the material becomes good when the material has the surface free energy in a predetermined range. If it deviates from the predetermined range the adhesive properties between the blood vessel cell and material is deteriorated. As such changes of the adhesive properties to a blood vessel cell due to the surface free energy, experimental results shown in Data, for instance, CMC Publishing Co., Ltd. "Biomaterial no Saisentan", Yoshito IKADA (editor), p. 109, lower part are known. As materials having the adhesive properties to a blood vessel cell owing to such a factor, for instance, hydrophilic polystyrene, and poly (N-isopropyl acrylamide) can be cited. When such a material is used, by the action of the photocatalyst upon irradiation with energy, for instance, a functional group on a surface of the material is substituted, decomposed or the like to cause a change in the surface free energy, resulting in one that does not have the adhesive properties to a blood vessel cell or one that has the cell adhesion-inhibiting properties.

When the adhesive properties between blood vessel cell and a material is determined owing to such as the electrostatic interaction, the adhesive properties to a blood vessel cell are determined by such as an amount of positive electric charges that the material has. As materials having the adhesive properties to a blood vessel cell owing to such electrostatic interaction, basic polymers such as polylysine; basic compounds such as aminopropyltriethoxysilane, N-(2-aminoethyl)-3-aminopropyltrimethoxysilane; and condensates and the like including these can be cited. When such materials are used, by the action of the photocatalyst upon irradiation with energy, the above-mentioned materials are decomposed or denatured. Thereby, for instance, an amount of positive electric charges present on a surface can be altered, resulting in one that does not have the adhesive properties to a blood vessel cell or one that has the cell adhesion-inhibiting properties.

As materials having the adhesive properties to a blood vessel cell owing to the biological characteristics, ones that are good in the adhesive properties with particular blood vessel cell or ones that are good in the adhesive properties with many blood vessel cells can be cited. Specifically, fibronectin, laminin, tenascin, vitronectin, RGD (arginine-glycine-asparagine acid) sequence containing peptide, YIGSR (tyrosine-isoleucine-glycine-serine-arginine) sequence containing peptide, collagen, atelocollagen, and gelatin can be cited. When such materials are used, by the action of the photocatalyst upon irradiation with energy, for instance, a structure of the material is partially destroyed, or a principal chain is destroyed, resulting in one that does not have the adhesive properties to a blood vessel cell or one that has the cell adhesion-inhibiting properties.

Such a blood vessel cell adhesive material, though it differs depending on the kind of the materials and the like, is comprised in the photocatalyst-containing cell adhesion layer normally in the range of 0.01% by weight to 95% by weight, and preferably in the range of 1% by weight to 10% by weight. Thereby, a region that contains the blood vessel cell adhesive material can be made a region good in the adhesive properties to a blood vessel cell.

(ii) Photocatalyst

Next, a photocatalyst contained in a photocatalyst-containing cell adhesion layer of the present embodiment will be explained below. As for a photocatalyst used in the present embodiment, it is not particularly limited as long as it is a photocatalyst that can decompose or denature the blood vessel cell adhesive material by the action of the photocatalyst accompanying with the energy irradiation.

Herein, the action mechanism of the photocatalyst which is represented by titanium oxide described later is not necessarily clear, however, it is considered that a carrier generated by the irradiation of the light changes the chemical structure of the organic material by the direct reaction with the compound nearby, or by the active oxygen species generated in the presence of water or oxygen. In the present embodiment, it is considered that this carrier has the influence on the blood vessel cell adhesive material described above.

As the photocatalyst that can be used in the present embodiment, specifically, for instance, titanium dioxide ($TiO_2$), zinc oxide (ZnO), tin oxide ($SnO_2$), strontium titanate ($SrTiO_3$), tungsten oxide ($WO_3$), bismuth oxide ($Bi_2O_3$) and iron oxide ($Fe_2O_3$) that are known as photo-semiconductors can be cited. These can be used singularly or in combination of at least two kinds.

In the present embodiment, in particular, titanium dioxide, owing to a large band gap, chemical stability, non-toxicity, and easy availability, can be preferably used. There are two types of titanium dioxide, anatase type and rutile type, and both can be used in the present embodiment; however, the anatase type titanium dioxide is more preferable. An excitation wavelength of the anatase type titanium dioxide is 380 nm or less.

As such anatase type titanium dioxide, for instance, an anatase titania sol of hydrochloric acid deflocculation type (trade name: STS-02, manufactured by ISHIHARA SANGYO KAISHA, LTD., average particle diameter: 7 nm, and trade name: ST-KO1, manufactured by ISHIHARA SANGYO KAISHA, LTD.), and an anatase titania sol of nitric acid deflocculation type (trade name: TA-15, manufactured by NISSAN CHEMICAL INDUSTRIES, LTD., average particle diameter: 12 nm) can be cited.

The smaller is a particle diameter of the photocatalyst, the better, because a photocatalyst reaction is caused more effectively. It is preferable to use the photocatalyst with an average particle diameter of 50 nm or less, and one having an average particle diameter of 20 nm or less can be particularly preferably used.

The contents of a photocatalyst in a photocatalyst-containing cell adhesion layer of the present embodiment can be set in the range from 5 to 95% by weight, preferably in the range from 10 to 60% by weight, and more preferably in the range from 20 to 40% by weight.

It is because this enables a blood vessel cell adhesive material in the area of the photocatalyst-containing cell adhesion layer where the energy has been irradiated to be decomposed or denatured.

Herein, as for a photocatalyst used in the present embodiment, it is preferable that its adhesive properties with blood vessel cells are low by, for example, having a high hydrophilicity. It is because this enables the area where the photocatalyst has been exposed by the blood vessel cell adhesive material being decomposed and so on to be used as an area where the adhesive properties with the blood vessel cells is low.

(iii) The Others

In this embodiment, not only the blood vessel cell adhesive material or the photocatalyst but also a binder etc. for improving such as strength or resistance may be contained as necessary in the photocatalyst-containing cell adhesion layer. In the present embodiment, particularly as the binder, a material that, at least after the energy irradiation, has the cell adhesion-inhibiting properties of inhibiting adhesion to the blood vessel cell is preferably used. This is because the adhesion between the blood vessel cell and the cell adhesion-inhibiting portion, which is a region irradiated with energy, can thereby be reduced. As such a material, for example, one that has the cell adhesion-inhibiting properties prior to the energy irradiation or one that obtains the cell adhesion-inhibiting properties by the action of the photocatalyst upon irradiation with energy may be used.

In the present embodiment, a material that becomes to have the cell adhesion-inhibiting properties, particularly by the action of the photocatalyst upon irradiation with energy, is preferably used as a binder. Thereby, in a region prior to the energy irradiation, the adhesive properties between the blood vessel cell adhesive material and the blood vessel cell is not inhibited, and only a region where energy is irradiated can be lowered in the adhesive properties to a blood vessel cell.

As materials that can be used as such a binder, for instance, ones in which a principal skeleton has such a high bond energy, that cannot be decomposed by the photo-excitation of the photocatalyst, and has an organic substituent which can be decomposed by an action of the photocatalyst are preferably used. For instance, (1) organopolysiloxane that exhibits large strength by hydrolyzing or polycondensating chloro- or alkoxysilane or the like owing to a sol-gel reaction and the like, and (2) organopolysiloxane and the like in which reactive silicones excellent in the water repellency or oil repellency are crosslinked can be cited. For example, those disclosed in JP-A No. 2000-249821 can be used.

When the above-mentioned material is used as the blood vessel cell adhesion-inhibiting material, the contact angle thereof with water is preferably in the range of 15° to 120°, more preferably 20° to 100° before the material is irradiated with energy. According to this, the adhesion of the blood vessel cell adhesive material to the blood vessel cell is not inhibited.

In the case of irradiating this blood vessel cell adhesion-inhibiting material with energy, it is preferred that the contact angle thereof with water becomes 10° or less. This range makes it possible to render the material having a high hydrophilicity and low adhesive properties to a blood vessel cell.

The contact angle with water referred to herein is a result obtained by using a contact angle measuring device (CA-Z model, manufactured by Kyowa Interface Science Co., Ltd.) to measure the contact angle of the material with water or a liquid having a contact angle equivalent to that of water (after 30 seconds from the time when droplets of the liquid are dropped down from its micro syringe), or a value obtained from a graph prepared from the result.

In the present embodiment, a decomposing material or the like that causes such as a change in the wettability of a region where energy is irradiated, thereby lowers the adhesive properties to a blood vessel cell or that aides such a change, or other kinds of additive agents may be contained.

As a decomposing material or an additive agent, for example, a material or an agent described in JP-A No. 2000-249821 can be used.

In the present embodiment, such a binder and the like can be preferably comprised in the photocatalyst-containing cell adhesion layer, in the range of 5% by weight to 95% by weight, more preferably 40% by weight to 90% by weight, and particularly preferably 60% by weight to 80% by weight.

Moreover, as a base material used in the present embodiment, it is not particularly limited as long as it is a base material capable of forming the photocatalyst-containing cell adhesion layer. As the base material described above, for example, an inorganic material such as a metal, a glass, or silicone and an organic material represented by a plastic can be used.

Moreover, the flexibility of a base material is appropriately selected. Moreover, the transparency of the base material is appropriately selected according to the direction of the irradiation of the energy irradiated for decomposing or denaturing the blood vessel cell adhesive material and the like. For example, in the case where the base material has the light shielding portion or the like and where the irradiation of the energy is performed from the side of the base material, it is made that the base material has the transparency.

Herein, in the present embodiment, in the case where the base material has the transparency for the energy irradiated, the light shielding portion may be formed in a form for forming the cell adhesion portion, specifically, in a form of the blood vessel forming pattern. It is because owing to this, at the time of forming the cell adhesion-inhibiting portion by irradiating the energy, the blood vessel cell adhesive material in the photocatalyst-containing cell adhesion layer only in the targeted area can be decomposed or denatured, without using such as a photomask, by irradiating the energy to the total surface from the rear surface side of the base material. As the light shielding portion described above, a light shielding portion similar to the light shielding portion generally used can be used, thus, the detailed explanation is not repeated here.

b. Forming Method of Cell Adhesion-Inhibiting Portion

Figure 3A:
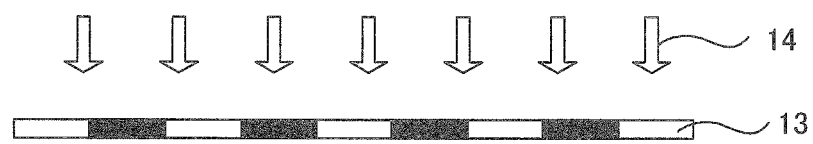
FIGS. 3A and 3B are illustrations for explaining one example of a process for forming a blood vessel cell culturing pattern in a manufacturing method of an artificial blood vessel of the present invention.
Figure 3A:
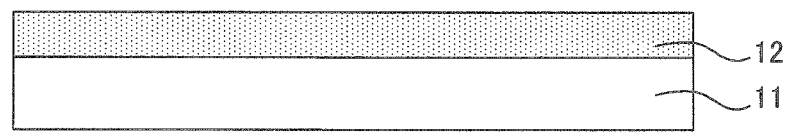
Figure 3B:
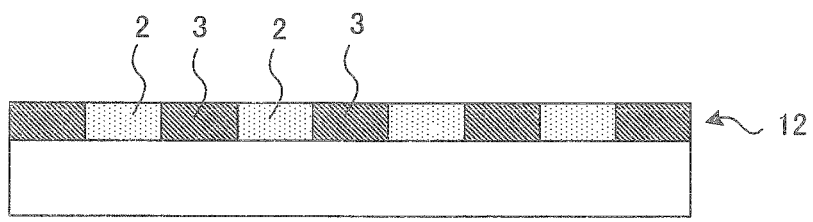

Next, a forming method of a cell adhesion-inhibiting portion in the present embodiment will be explained below. In the present embodiment, for example, as shown in FIGS. 3A and 3B; the blood vessel cell adhesive material in the photocatalyst-containing cell adhesion layer 12 in the area where the energy has been irradiated is decomposed or denatured, the cell adhesion-inhibiting portion 3 which does not have the adhesive properties with the blood vessel cells can be formed and it can be made that the area where the energy has not been irradiated the cell adhesion portion (FIG. 3B), by irradiating the energy 14 on the photocatalyst-containing cell adhesion layer 12 formed on the base material 11 using such as the photomask 13 having the light shielding portion in a form of the blood vessel formation pattern (FIG. 3A). At this time, in the cell adhesion-inhibiting portion, the photocatalyst and the decomposed material or the denatured material the blood vessel cell adhesive material are contained.

The energy irradiation (exposure) mentioned in this embodiment is a concept that includes all energy ray irradiation that can decompose or denature the blood vessel cell adhesive material by the action of the photocatalyst upon irradiation with energy, and is not limited to light irradiation.

Normally, as the light used in such energy irradiation, the wavelength of the light is set in the range of 400 nm or less, preferably 380 nm or less. This is because, as mentioned above, the photocatalyst that is preferably used as a photocatalyst is titanium dioxide, and as energy that activates a photocatalyst action by the titanium oxide, the light having the above-mentioned wavelength is preferable.

As a light source that can be used in such energy irradiation, a mercury lamp, metal halide lamp, xenon lamp, excimer lamp and other various kinds of light sources can be cited.

Other than the method in which pattern irradiation is carried out via a photomask by using the above-mentioned light source, a method of carrying out drawing irradiation in a pattern by using laser such as excimer or YAG can be applied. Furthermore, as mentioned above, when the base material has the light-shielding portion in a pattern same as that of the cell adhesion portion, energy can be irradiated over the entire surface from the base material side. In this case, there are advantages in that there are no needs of the photomask and the like and a process of positional alignment and the like are also not necessary.

An amount of irradiation of energy at the energy irradiation is an amount of irradiation necessary for decomposing or denaturing the blood vessel cell adhesive material by the action of the photocatalyst.

At this time, by energy irradiating a layer containing the photocatalyst while heating, the sensitivity can be raised; accordingly, it is preferable in that the blood vessel cell adhesive material can be efficiently decomposed or denatured. Specifically, it is preferable to heat in the range of 30° C. to 80° C.

The energy irradiation that is carried out via a photomask in this embodiment, when the above-mentioned base material is transparent, may be carried out from either direction of the base material side or a photocatalyst-containing cell adhesion layer side. On the other hand, when the base material is opaque, it is necessary to irradiate energy from a photocatalyst-containing cell adhesion layer side.

(2) Second Embodiment

Next, as a second embodiment, the cell culturing layer is a photocatalyst-containing cell adhesion-inhibiting layer containing at least a photocatalyst, and a blood vessel cell adhesion-inhibiting material having the cell adhesion-inhibiting properties for inhibiting the adhesion with the blood vessel cell and decomposed or denatured by the action of the photocatalyst accompanying with the energy irradiation; and it is a case where a cell adhesion portion is formed by decomposing or denaturing the blood vessel cell adhesion-inhibiting material by irradiating the energy on the photocatalyst-containing cell adhesion-inhibiting layer, for example, using a photomask having the opening portion in a pattern form of the blood vessel formation pattern.

In the present embodiment, since the photocatalyst-containing cell adhesion-inhibiting layer contains the photocatalyst and the blood vessel cell adhesion-inhibiting material, the blood vessel cell adhesion-inhibiting material can be decomposed or denatured and the area where the energy has been irradiated can be made as a cell adhesion portion having the adhesive properties with the blood vessel cells, through the action of the photocatalyst contained in the layer by irradiating the energy in a pattern form of the blood vessel formation pattern on the area where the cell adhesion portion is formed. Moreover, at this time, as for the area where the energy is not irradiated, the blood vessel cell adhesion-inhibiting material still remains, and it can be made as the cell adhesion-inhibiting portion.

Hereinafter, a photocatalyst-containing cell adhesion-inhibiting layer and a base material used in the present embodiment will be explained, and further, a forming method of a cell adhesion portion will be explained below.

a. Photocatalyst-Containing Cell Adhesion-Inhibiting Layer

First, a photocatalyst-containing cell adhesion-inhibiting layer used in the present embodiment will be explained below. A photocatalyst-containing cell adhesion-inhibiting layer used in the present embodiment is a layer containing the photocatalyst and the blood vessel cell adhesion-inhibiting material, and it is to be a layer having the adhesive properties with the blood vessel cells by decomposing or denaturing the blood vessel cell adhesion-inhibiting material through the action of the photocatalyst accompanying with the energy irradiation.

The formation of the above-described photocatalyst-containing cell adhesion-inhibiting layer can be performed by, for example, coating on the base material a coating solution for forming the photocatalyst-containing cell adhesion-inhibiting layer containing the blood vessel cell adhesion-inhibiting material which is decomposed or denatured by the action of the photocatalyst accompanying with the energy irradiation and the photocatalyst. The coating of the coating solution for forming the photocatalyst-containing cell adhesion-inhibiting layer can be performed by utilizing a general method of coating such as a spin coat method, a spray coat method, a dip coat method, a roll coat method, and a bead coat method At this time, as the thickness of the film of the photocatalyst-containing cell adhesion-inhibiting layer, it is usually in the range from about 0.01 μm to about 1.0 μm, and particularly in the range form about 0.1 μm to about 0.3 μm.

Hereinafter, a material used in the photocatalyst-containing cell adhesion-inhibiting layer will be explained below. Since the photocatalyst used in the present embodiment can be similar to the photocatalyst used in the above-described first embodiment, the detailed explanation is not repeated here.

(i) Blood Vessel Cell Adhesion-Inhibiting Material

First, a blood vessel cell adhesion-inhibiting material contained in the photocatalyst-containing cell adhesion-inhibiting layer used in the present embodiment will be explained below.

As for a blood vessel cell adhesion-inhibiting material used in the present embodiment, the kind of it and other properties is not particularly limited if it is a blood vessel cell adhesion-inhibiting material having the cell adhesion-inhibiting properties for inhibiting the adhesion with the blood vessel cells and it is decomposed or denatured by the action of the photocatalyst accompanying with the energy irradiation.

For the blood vessel cell adhesion-inhibiting material used in the present embodiment, those having the above-described cell adhesion-inhibiting properties in which the cell adhesion-inhibiting properties are lost or become to show the cell adhesive properties by being decomposed or denatured by the action of the photocatalyst accompanying with the energy irradiation can be used.

As the blood vessel cell adhesion-inhibiting material, a material having high hydration ability can be used as an example. The material having high hydration ability forms a hydration layer wherein water molecules gather around thereof. Usually, since such a material having high hydration ability has higher adhesion to water molecules than adhesion to the blood vessel cell, the blood vessel cell cannot be adhered to the material having high hydration ability. Thus, the layer will have low adhesive properties to the blood vessel cell. The hydration ability is referred to as a property of hydrating with water molecules, and high hydration ability is intended to mean that the material is easily hydrated with water molecules.

As the material having high hydration ability and is used as a blood vessel cell adhesion-inhibiting material, for example, polyethylene glycol, amphoteric ionic materials having a betaine structure, or phospholipid-containing materials can be listed. When such materials are used as the blood vessel cell adhesion-inhibiting material, upon irradiated with energy in the below-described energy irradiating process, the blood vessel cell adhesion-inhibiting material is decomposed or denatured by the action of a photocatalyst so as to remove the hydration layer on the surface, thereby obtaining the material not having the cell adhesion-inhibiting properties.

In this embodiment, a surfactant, which is decomposed by the action of a photocatalyst and has water repellent or oil repellent organic substituent, can also be used as the blood vessel cell adhesion-inhibiting material. As such surfactant for example, nonionic surfactants such as: hydrocarbon based such as the respective series of NIKKOL BL, BC, BO, and BB manufactured by Nikko Chemicals Co., Ltd.; and fluorine based or silicone based such as ZONYL FSN and FSO manufacture by Du Pont Kabushiki Kaisha, Surflon S-141 and 145 manufactured by ASAHI GLASS CO., LTD., Megaface F-141 and 144 manufactured by DAINIPPON INK AND CHEMICALS, Inc., FTERGENT F-200 and F251 manufactured by Neos, UNIDYNE DS-401 and 402 manufactured by DAIKIN INDUSTRIES, Ltd., and Fluorad FC-170 and 176 manufactured by 3M can be cited. Also, cationic surfactants, anionic surfactants and amphoteric surfactants also can be used.

When the photocatalyst-containing cell adhesion-inhibiting layer is formed by using the above material as the blood vessel cell adhesion-inhibiting material, the blood vessel cell adhesion-inhibiting material is unevenly distributed on the surface. The water repellency or oil repellency on the surface can thereby be increased, and the interaction with the blood vessel cell can be decreased to reduce adhesive properties to the blood vessel cell. Upon irradiation of this layer with energy in the energy irradiating process, the material is easily decomposed by the action of the photocatalyst to expose the photocatalyst. Thus, one not having the cell adhesion-inhibiting properties can be obtained.

In this embodiment, a material, which obtains good adhesive properties to a blood vessel cell by the action of the photocatalyst upon irradiation with energy, is particularly preferably used as the blood vessel cell adhesion-inhibiting material. As such blood vessel cell adhesion-inhibiting material, for example, materials having oil repellency or water repellency can be listed.

When the material having oil repellency or water repellency is used as the blood vessel cell adhesion-inhibiting material, the interaction such as hydrophobic interaction between the blood vessel cell and the blood vessel cell adhesion-inhibiting material is made low by the water repellency or oil repellency of the blood vessel cell adhesion-inhibiting material, thereby decreasing adhesive properties to the blood vessel cell.

As the material having water repellency or oil repellency, a material, for example, which has such high bonding energy that the skeleton thereof is not decomposed by the action of the photocatalyst and has water repellent or oil repellant organic substituent to be decomposed by action of the photocatalyst, can be listed.

Examples of such a material, which has such high bonding energy that the skeleton thereof is not decomposed by the action of the photocatalyst and has water repellent or oil repellant organic substituent to be decomposed by action of the photocatalyst, include, for example, the materials used as the binder in the first embodiment, that is, (1) the organopolysiloxanes exhibiting high strength, obtained by hydrolyzing or polycondensating chloro- or alkoxysilanes by sol-gel reaction etc., and (2) organopolysiloxanes obtained by crosslinking reactive silicone.

When such material is used as the binder in the first embodiment, the material is used as a material having cell adhesion-inhibiting properties by decomposing or denaturing the side chains of the organopolysiloxanes, in high ratio, so as to make it super hydrophilic by the action of the photocatalyst upon irradiation with energy. However, in this embodiment, the region irradiated with the energy can have adhesive properties to a blood vessel cell by irradiating with energy to such a degree that side chains of the organopolysiloxanes are not completely decomposed or denatured by the action of the photocatalyst upon irradiation with energy. Together with the above-mentioned organopolysiloxanes, a stable organosilicon compound not undergoing any crosslinking reaction, such as dimethylpolysiloxane, can also be separately mixed.

When the material having water repellency or oil repellency is used as the blood vessel cell adhesion-inhibiting material, the material preferably has a contact angle, with water, of 80° or more, particularly in the range of 100° to 130°. With this contact angle given, the adhesive properties to a blood vessel cell of the photocatalyst-containing cell adhesion-inhibiting layer before irradiation with energy can be reduced. The upper limit of the angle is the upper limit of the contact angle, with water, of the blood vessel cell adhesion-inhibiting material on a flat base material. For example, when the contact angle, with water, of the blood vessel cell adhesion-inhibiting material on a base material with concavoconvex is measured, the upper limit may be about 160° as shown by Ogawa et al. in Japanese Journal of Applied Physics, Part 2, Vol. 32, L614-L615, 1993.

When this blood vessel cell adhesion-inhibiting material is irradiated with energy to impart the adhesive properties to the blood vessel cell, the material is preferably irradiated with energy such that the contact angle thereof with water comes to be in the range of 10° to 40°, particularly 15° to 30°. The adhesive properties to the blood vessel cell of the photocatalyst-containing cell adhesion-inhibiting layer after energy irradiation can thereby be increased. The contact angle with water can be obtained by the method described above.

The blood vessel cell adhesion-inhibiting material is contained preferably in the range of 0.01% by weight to 95% by weight, particularly 1% by weight to 10% by weight, in the photocatalyst-containing cell adhesion-inhibiting layer. The region containing the cell adhesion-inhibiting material can thereby be a region of low adhesive properties to the blood vessel cell.

The cell adhesion-inhibiting material preferably has surface activity. For example, when drying the photocatalyst-containing cell adhesion-inhibiting layer-forming coating solution containing the blood vessel cell adhesion-inhibiting material after coating thereof, the material is distributed highly unevenly on the surface of the coating film, thus giving excellent cell adhesion-inhibiting properties.

(ii) Others

The photocatalyst-containing cell adhesion-inhibiting layer in this embodiment may contain a binder and the like in accordance with required characteristics such as coating properties in formation of the layer, strength and resistance of the formed layer. The blood vessel cell adhesion-inhibiting material may also function as the binder.

As the binder, for example, a binder having such high bonding energy that its principal skeleton is not decomposed by the action of the photocatalyst can be used. Specific examples of the binder include such as polysiloxane not having organic substituents or having organic substituents to such a degree that adhesive properties are not adversely affected, and such polysiloxane can be obtained by hydrolyzing or polycondensating such as tetramethoxysilane or tetraethoxysilane.

In this embodiment, the binder is contained preferably in the range of 5% by weight to 95% by weight, more preferably 40% by weight to 90% by weight, still more preferably 60% by weight to 80% by weight, in the photocatalyst-containing cell adhesion-inhibiting layer. By incorporation of the binder in this range, formation of the photocatalyst-containing cell adhesion-inhibiting layer can be facilitated and the photocatalyst-containing cell adhesion-inhibiting layer can be endowed with strength etc., thus allowing it to exhibit its characteristics.

In this embodiment, the photocatalyst-containing cell adhesion-inhibiting layer preferably contains a blood vessel cell adhesive material having adhesive properties to the blood vessel cell, at least after irradiation with energy. By this, in the photocatalyst-containing cell adhesion-inhibiting layer, adhesive properties to the blood vessel cell of the cell adhesion portion, which is the region irradiated with energy, can be further improved. The blood vessel cell adhesive material may be a material usable as the binder or may be a material used separately from the binder. The blood vessel cell adhesive material may have good adhesive properties to the blood vessel cell prior to irradiation with energy, or may be endowed with good adhesive properties to the blood vessel cell by the action of the photocatalyst upon irradiation with energy.

In this embodiment, as long as the blood vessel cell adhesive material have good adhesive properties to a blood vessel cell at least after being irradiated with energy, the adhesive properties to a blood vessel cell can be improved, for example, by biological characteristics or by physical interaction such as hydrophobic interaction, electrostatic interaction, hydrogen bonding, and van der Waals force.

In this embodiment, the blood vessel cell adhesive material is contained preferably in the range of 0.01% by weight to 95% by weight, particularly 1% by weight to 10% by weight, in the photocatalyst-containing cell adhesion-inhibiting layer. By this, the photocatalyst-containing cell adhesion-inhibiting layer can further improve the adhesive properties to the blood vessel cell of the cell adhesion portion, which is a region irradiated with energy. When the material having good adhesive properties to the blood vessel cell prior to irradiation with energy is used as the blood vessel cell adhesive material, the material is preferably contained to such a degree as not to inhibit the cell adhesion-inhibiting properties of the blood vessel cell adhesion-inhibiting material in the region not irradiated with energy, that is, the region serving as the cell adhesion-inhibiting portion.

Moreover, as for the base material used in the present embodiment, it is not particularly limited if it is a base material which is capable of forming the above-described photocatalyst-containing cell adhesion-inhibiting layer, and it can be made the base material w explained in the first embodiment.

Herein, in the present embodiment, in the case where the base material has the transparency for the energy to be irradiated, the light shielding portion may be formed in the area where it is made the cell adhesion-inhibiting portion. It is because owing to this, at the time when it is made cell adhesion portion by irradiating the energy on the photocatalyst-containing cell adhesion-inhibiting layer, it is not necessary to use a photomask or the like, the cell adhesion portion can be easily formed by irradiating the energy on the whole surface from the rear surface of the base material.

Herein, as for the kind of a base material, a forming method of the above-described light shielding portion and the kind thereof used in the present embodiment, since it is similar to these explained in the first embodiment, the detailed explanation is not repeated here.

b. Forming Method of Cell Adhesion Portion

Next, a forming method of a cell adhesion portion will be explained below. In the present embodiment, the energy is irradiated on the photocatalyst-containing cell adhesion-inhibiting layer, for example, using a photomask having the opening portion in a form of the blood vessel formation pattern. It is because owing to this, the cell adhesion-inhibiting material in the area where the energy has been irradiated can be decomposed or denatured t to make the cell adhesion portion having the adhesive properties with the blood vessel cell. At the time, a photocatalyst, the decomposed material or the denatured material of the blood vessel cell adhesion-inhibiting material and the like are contained in the cell adhesion portion. On the other hand, the blood vessel cell adhesion-inhibiting material which is the area where the energy is not irradiated remains, and it can be made cell adhesion-inhibiting portion not having the adhesive properties with the blood vessel cell.

As for the above-described method of irradiating the energy or the like, the detailed explanation is not repeated here since it is similar to these explained in the first embodiment described above.

(3) Third Embodiment

Next, as a third embodiment; the cell culturing layer is a blood vessel cell adhesion layer having the adhesive properties with the blood vessel cell and containing a blood vessel cell adhesive material decomposed or denatured by the action of the photocatalyst accompanying with the energy irradiation, formed on the photocatalyst-containing layer containing at least a photocatalyst; and it is a case where a cell adhesion-inhibiting portion is formed on the blood vessel cell adhesion layer by decomposing or denaturing the blood vessel cell adhesive material by irradiating the energy using for example a photomask having the light shielding portion in a pattern form of the blood vessel formation pattern.

In the present embodiment, since the blood vessel cell adhesion layer is formed on the photocatalyst-containing layer by the energy irradiation, the blood vessel cell adhesive material in the blood vessel cell adhesion layer is decomposed or denatured by the action of the adjoined photocatalyst in the photocatalyst-containing layer to enable to form the cell adhesion-inhibiting portion whose adhesive properties with the blood vessel cells in the area has been lowered. At this time, in the case where for example, the blood vessel cell adhesive material is decomposed by the action of the photocatalyst accompanying with the energy irradiation, the small amount of the blood vessel cell adhesive material is contained in the cell adhesion-inhibiting portion the decomposed material of the blood vessel cell adhesive material or the like is contained, or the photocatalyst-containing layer is exposed and so on by completely decomposing and removing the blood vessel cell adhesion layer. Moreover, in the case where the blood vessel cell adhesive material is denatured by the action of the photocatalyst accompanying with the energy irradiation, the denatured material or the like is contained in the cell adhesion-inhibiting portion.

Moreover, according to the present embodiment, in the process for culturing a blood vessel cell described later, at the time when the blood vessel cells are attached to the cell adhesion portion, cultured and made into a tissue, the blood vessel cells which have been attached to the cell adhesion-inhibiting portion can be removed and so on by the action of the photocatalyst by irradiating the energy to the cell adhesion-inhibiting portion. Owing to this, it has also an advantage that blood vessels in a further finely processed pattern can be formed.

Hereinafter, the respective constitutions of the present embodiment will be explained below. The base material and the forming method of a cell adhesion-inhibiting portion used in the present embodiment are similar to the first embodiment, and the explanation is not repeated here.

a. Blood Vessel Cell Adhesion Layer

First, a blood vessel cell adhesion layer used in the present embodiment will be explained below. The blood vessel cell adhesion layer used in the present embodiment is a layer having a blood vessel cell adhesive material having at least the adhesive properties with the cell and layers generally used as a layer having the adhesive properties with the blood vessel cells can be used.

As a specific blood vessel cell adhesive material, since a cell adhesive material similar to the blood vessel cell adhesive material used in the photocatalyst-containing cell adhesion layer explained in the first embodiment can be used, the detailed explanation is not repeated here. Moreover, it is preferable that a material having the cell adhesion-inhibiting properties explained in the photocatalyst-containing cell adhesion layer which has been explained in the first embodiment is also contained in the blood vessel cell adhesion layer of this embodiment. Owing to this, it becomes possible that the adhesive properties with the blood vessel cell of the cell adhesion-inhibiting portion which is the energy-irradiated area is lowered.

Moreover, as for the formation of the blood vessel cell adhesion layer, it can performed by coating a coating solution for forming a blood vessel cell adhesion layer containing the blood vessel cell adhesive material by a general coating method. Since it can be made similar to a forming method of the photocatalyst-containing cell adhesion layer of the first embodiment, the explanation is repeated here. It should be noted that in the case where a blood vessel cell adhesive material, such as protein, comparatively expensive, there may be a case where the absorption method is applied to the formation of the blood vessel cell adhesion layer.

The thickness of the film of the blood vessel cell adhesion layer could be made in the range from about 0.01 µm to about 1.0 µm, and particularly in the range from about 0.01 µm to about 0.3 µm.

b. Photocatalyst-Containing Layer

Next, a photocatalyst-containing layer used in the present embodiment will be explained below. As for a photocatalyst-containing layer used in the present embodiment, it is not particularly limited as long as it is a layer containing at least photocatalyst. For example, it may be a layer comprising only photocatalyst, or a layer containing the other component such as binder.

As a photocatalyst used in the present embodiment, it is preferable that it can be made similar to the photocatalyst used in the photocatalyst-containing cell adhesion layer in the first embodiment and particularly titanium oxide is used also in the present embodiment.

Here, in the case where a photocatalyst-containing layer comprising only a photocatalyst has been used, the efficiency concerning with the decomposition or the denaturation of the blood vessel cell adhesive material in the blood vessel cell adhesion layer is enhanced, and it has the advantages from the viewpoint of the cost such as by shortening the treatment time. On the other hand, in the case where a photocatalyst-containing layer comprising a photocatalyst and a binder has been used, it has the advantage that the formation of the photocatalyst-containing layer is easy.

An example of the forming method for the photocatalyst-containing layer made only of a photocatalyst may be a vacuum film-forming method such as sputtering, CVD or vacuum vapor deposition. The formation of the photocatalyst-containing layer by the vacuum film-forming method makes it possible to render the layer a homogeneous photocatalyst-containing layer made only of a photocatalyst. Thereby, the blood vessel cell adhesive material can be decomposed or denatured homogeneously. At the same time, since the layer is made only of a photocatalyst, the blood vessel cell adhesive material can be decomposed or denatured more effectively, as compared to the case of using also a binder.

Another example of the method for forming the photocatalyst-containing layer made only of a photocatalyst, is the following method: for example, in the case that the photocatalyst is titanium dioxide, amorphous titania is formed on the base material, and then, calcinating so as to phase-change the titania to crystalline titania. The amorphous titania used in this case can be obtained, for example, by hydrolysis or dehydration condensation of an inorganic salt of titanium, such as titanium tetrachloride or titanium sulfate, or hydrolysis or dehydration condensation of an organic titanium compound, such as tetraethoxytitanium, tetraisopropoxytitanium, tetra-n-propoxytitanium, tetrabutoxytitanium or tetramethoxytitanium, in the presence of an acid. Next, the resultant is calcinated at 400° C. to 500° C. so as to be denatured to anatase type titania, and calcinated at 600° C. to 700° C. so as to be denatured to rutile type titania.

In the case of using a binder, the binder preferably having a high bonding energy, wherein its principal skeleton is not decomposed by photoexcitation of the photocatalyst is used. Examples of such a binder include the organopolysiloxanes described in the above-mentioned item "Blood vessel cell adhesion layer".

In the case of using such organopolysiloxanes as the binder, the photocatalyst-containing layer can be formed by dispersing a photocatalyst, the organopolysiloxane as the binder, and optional additives if needed into a solvent to prepare a coating solution, and coating this coating solution onto the base material. The used solvent is preferably an alcoholic based organic solvent such as ethanol or isopropanol. The coating can be performed by a known coating method such as spin coating, spray coating, dip coating, roll coating, or bead coating. When the coating solution contains an ultraviolet curable component as the binder, the photocatalyst-containing layer can be formed by curing the coating solution through the irradiation of ultraviolet rays.

As the binder, an amorphous silica precursor can be used. This amorphous silica precursor is preferably a silicon compound represented by the general formula $SiX_4$, wherein X being halogen, methoxy group, ethoxy group, acetyl group or the like; silanol which is a hydrolyzate thereof; or polysiloxane having an average molecular weight of 3000 or less.

Specific examples thereof include such as tetraethoxysilane, tetraisopropoxysilane, tetra-n-propoxysilane, tetrabutoxysilane, and tetramethoxysilane. In this case, the photocatalyst-containing layer can be formed by dispersing the amorphous silica precursor and particles of a photocatalyst homogeneously into a non-aqueous solvent, hydrolyzing with water content in the air to form a silanol onto a transparent base material, and then subjecting to dehydration polycondensation at room temperature. When the dehydration polycondensation of the silanol is performed at 100° C. or higher, the polymerization degree of the silanol increases so that the strength of the film surface can be improved. A single kind, or two or more kinds of this binding agent may be used.

The content of the photocatalyst in the photocatalyst-containing layer can be set in the range of 5 to 60% by weight, preferably in the range of 20 to 40% by weight. The thickness of the photocatalyst-containing layer is preferably in the range of 0.05 to 10 μm.

Besides the above-mentioned photocatalyst and binder, the surfactant and so on used in the above-mentioned blood vessel cell adhesion layer can be incorporated into the photocatalyst-containing layer.

Here, in the present embodiment, as for the photocatalyst-containing layer, it is preferable that on the surface, the adhesive properties with the cells is low because the surface is hydrophilic and the like. Owing to this, in the case where the blood vessel cell adhesion layer is decomposed and so on, and the photocatalyst-containing layer is exposed, the area can be made an area where the adhesive properties with the cells is low.

Moreover, in the present embodiment, the light shielding portion may be formed on the photocatalyst-containing layer in a pattern of forming the cell adhesion portion, specifically, in a pattern form of the blood vessel formation pattern. It is because owing to this, in the case where the energy has been irradiated on the whole surface of the blood vessel cell adhesion layer, the photocatalyst on the area where the light shielding portion has been formed is not excited, the blood vessel cell adhesive material contained in the blood vessel cell adhesion layer other than the area where the light shielding portion has been formed can be decomposed or denatured. Moreover, in this case, since the photocatalyst in the area where the light shielding portion has been formed is not excited, it has an advantage that the direction of the energy being irradiated is not particularly limited.

As the above-described light shielding portion, since it is possible that a light shielding portion similar to the light shielding portion explained in the first embodiment is used, the detailed explanation is not repeated here.

(4) Fourth Embodiment

Next, as a fourth embodiment, the cell culturing layer is a blood vessel cell adhesion-inhibiting layer containing a blood vessel cell adhesion-inhibiting material having the cell adhesion-inhibiting properties for inhibiting the adhesion to the cell and decomposed or denatured by the action of the photocatalyst accompanying with the energy irradiation; and it is formed on the photocatalyst-containing layer of the blood vessels containing at least a photocatalyst, and it is the case where the blood vessel cell adhesion-inhibiting material is decomposed or denatured by irradiating the energy on the blood vessel cell adhesion-inhibiting layer using a photomask and the like having the opening portion, for example, in a pattern form of the blood vessel formation pattern to form the cell adhesion portion.

In the present embodiment, since blood vessel the cell adhesion-inhibiting layer has been formed on the photocatalyst-containing layer, the photocatalyst contained in the photocatalyst-containing layer is excited, the blood vessel cell adhesion-inhibiting material in the blood vessel cell adhesion-inhibiting layer can be decomposed or denatured, and the cell adhesion portion can be formed by irradiating the energy in a pattern form of the blood vessel formation pattern on the blood vessel cell adhesion-inhibiting layer. Moreover, at this time, the area where the energy is not irradiated and the cell adhesion-inhibiting material remains can be made the cell adhesion-inhibiting portion.

Here, the fact that the blood vessel cell adhesion-inhibiting material is decomposed or denatured means that the blood vessel cell adhesion-inhibiting material is not contained, or the less amount of the blood vessel cell adhesion-inhibiting material is contained when it is compared to the amount of the blood vessel cell adhesion-inhibiting material contained in the cell adhesion-inhibiting portion. For example, in the case where the blood vessel cell adhesion-inhibiting material is decomposed by the action of the photocatalyst accompanying with the energy irradiation, it means that the small amount of the blood vessel cell adhesion-inhibiting material is contained in the cell adhesion portion, the decomposed material of the blood vessel cell adhesion-inhibiting material or the like is contained, or the blood vessel cell adhesion-inhibiting material is completely decomposed and the photocatalyst-containing layer is exposed. Moreover, in the case where the blood vessel cell adhesion-inhibiting material is denatured by the action of the photocatalyst accompanying with the energy irradiation, the denatured material or the like is contained in the cell adhesion portion. In the present embodiment, it is preferable that the cell adhesion material having the adhesive properties with the blood vessel cell is contained in the above-described cell adhesion portion at least after the energy has been irradiated. It is because owing to this, that the adhesive properties with the blood vessel cell of the cell adhesion portion can be made higher, and it becomes possible that the blood vessel cell is adhered to only the cell adhesion portion in a highly fine process.

Hereinafter, a blood vessel cell adhesion-inhibiting layer used in the present embodiment will be explained below. As for the photocatalyst-containing layer used in the present embodiment, a photocatalyst-containing layer similar to the photocatalyst-containing layer explained in the third embodiment can be used; and as for the base material and the forming method of a cell adhesion portion used in the present embodiment, these similar to the second embodiment can be used. Therefore, the explanation is not repeated here.

a. Blood Vessel Cell Adhesion-Inhibiting Layer

As for a blood vessel cell adhesion-inhibiting layer used in the present embodiment, if it is formed on the photocatalyst-containing layer, has the cell adhesion-inhibiting properties for inhibiting the adhesion to the blood vessel cell, and contains the blood vessel cell adhesion-inhibiting material decomposed or denatured by the action of the photocatalyst accompanying with the energy irradiation, it is not particularly limited.

In the present embodiment, if the above-described layer can be formed, as for a forming method or the like is not particularly limited. It can be, for example, formed by coating a coating solution for forming the blood vessel cell adhesion-inhibiting layer containing the blood vessel cell adhesion-inhibiting material on the photocatalyst-containing layer by a general method of coating. Moreover, the thickness of the film of the blood vessel cell adhesion-inhibiting layer can be made that it is usually in the range from about 0.01 μm to about 1.0 μm, and particularly in the range from about 0.1 pinto about 0.3 μm.

Here, as a specific blood vessel cell adhesion-inhibiting material used for the blood vessel cell adhesion-inhibiting layer formed in the present embodiment, since a cell adhesion-inhibiting material similar to the blood vessel cell adhesion-inhibiting material used for the photocatalyst-containing cell adhesion-inhibiting layer explained in the first embodiment can be used, the detailed explanation is not repeated here. Moreover, it is preferable that a material having the cell adhesive properties explained in the photocatalyst-containing cell adhesion-inhibiting layer used in the second embodiment is contained also in the blood vessel cell adhesion-inhibiting layer of the present embodiment. It is because that owing to this, the adhesive properties with the cells of the cell adhesion portion which is the energy irradiated area can be made higher.

(5) Fifth Embodiment

Moreover, as a fifth embodiment, the cell culturing layer is a blood vessel cell adhesion layer containing a blood vessel cell adhesive material having the adhesive properties with the blood vessel cell and decomposed or denatured by the action of the photocatalyst accompanying with the energy irradiation in which; and it is a case where the blood vessel cell adhesion layer and the photocatalyst-containing layer containing a photocatalyst are disposed to oppose to each other and the energy is irradiated using, for example, a photomask having the light shielding portion in a pattern form of the blood vessel formation pattern to form the cell adhesion-inhibiting portion is formed by decomposing or denaturing the blood vessel cell adhesive material.

In the present embodiment, the blood vessel cell adhesive material in the blood vessel cell adhesion layer is decomposed or denatured to enable to form the cell adhesion-inhibiting portion by disposing the blood vessel cell adhesion layer and the photocatalyst-containing layer opposed each other, irradiating the energy in a pattern form for forming the cell adhesion-inhibiting portion, and by the action of the photocatalyst in the photocatalyst-containing layer.

Moreover, according to the present embodiment, in the blood vessel cell culturing process described later, at the time when the blood vessel cells are adhered to, cultured on the cell adhesion portion and made into a tissue, the blood vessel cells adhered to the cell adhesion-inhibiting portion can be removed and so on by the action of the photocatalyst by irradiating the energy on the cell adhesion-inhibiting portion. Owing to this, it has an advantage that the blood vessels can be formed in a further finely processed pattern.

Hereinafter, a photocatalyst-containing layer side substrate, and a forming method of a cell adhesion-inhibiting portion using the photocatalyst-containing layer side substrate used in the present embodiment will be explained below. As for the blood vessel cell adhesion layer used in the present embodiment, it is similar to the third embodiment, and the explanation is not repeated here.

a. Photocatalyst-Containing Layer Side Substrate

First, the photocatalyst-containing layer side substrate, comprising a photocatalyst-containing layer containing a photocatalyst, used in this embodiment is described. The photocatalyst-containing layer side substrate used in this embodiment usually comprises a photocatalyst-containing layer containing a photocatalyst and generally comprises a base body and a photocatalyst-containing layer formed on the base body. This photocatalyst-containing layer side substrate may also have, for example, photocatalyst-containing layer side light-shielding portion formed in a pattern form or a primer layer. The following will describe each of the constituents of the photocatalyst-containing layer side substrate used in this embodiment.

(i) Photocatalyst-Containing Layer

First, the photocatalyst-containing layer used in the photocatalyst-containing layer side substrate is described. The photocatalyst-containing layer used in this embodiment is not particularly limited insofar as the layer is constituted such that the photocatalyst in the photocatalyst-containing layer can cause the decomposition or denaturation of the blood vessel cell adhesive material in the adjacent blood vessel cell adhesion layer. The photocatalyst-containing layer may be composed of a photocatalyst and a binder or may be made of a photocatalyst only. The property of the surface thereof may be lyophilic or repellent to liquid.

Moreover, a photocatalyst-containing layer used in the present embodiment may be formed on the whole surface of the base body, or it may be formed on the pattern. It is because that: by forming the photocatalyst-containing layer in a pattern form, the pattern irradiation using a photomask or the like is not needed at the time when the energy is irradiated to form the cell adhesion-inhibiting portion; and the cell adhesion-inhibiting portion in which the blood vessel cell adhesive material contained in the blood vessel cell adhesion layer has been decomposed or denatured can be formed by irradiating the energy on the whole surface. The method of patterning the photocatalyst-containing layer is not particularly limited, and the patterning can be performed with a method such as a photolithography.

Moreover, since only the portion on the blood vessel cell adhesion layer facing to the photocatalyst-containing layer of the blood vessel cell adhesive material is actually decomposed or denatured if the energy is irradiated on the portion where the photocatalyst-containing layer and the blood vessel cell adhesion layer face each other, the energy may be irradiated from every direction. Further, it has an advantage that the irradiated energy is not particularly limited to parallel one such as parallel light.

Here, as for the photocatalyst-containing layer used in the present embodiment, it is possible that a photocatalyst-containing layer similar to the photocatalyst-containing layer explained in the third embodiment is used, thus the detailed explanation is not repeated here.

(ii) Base Body

The following will describe the base body used in the photocatalyst-containing layer side substrate. Usually, the photocatalyst-containing layer side substrate comprises at least a base body and a photocatalyst-containing layer formed on the base body. In this case, the material which constitutes the base body to be used is appropriately selected depending on the direction of energy irradiation which will be detailed later, necessity of the resulting pattern-forming body to be transparency, or other factors.

The base body used in this embodiment may be a member having flexibility, such as a resin film, or may be a member having no flexibility, such as a glass substrate. This is appropriately selected depending on the method of the energy irradiation.

An anchor layer may be formed on the base body in order to improve the adhesion between the surface of the base body and the photocatalyst-containing layer. The anchor layer may be made of, for example, a silane based or titanium based coupling agent.

(iii) Photocatalyst-Containing Layer Side Light-Shielding Portion

The photocatalyst-containing layer side substrate used in this embodiment may be a photocatalyst-containing layer side substrate on which photocatalyst-containing layer side light-shielding portion is formed in a pattern of blood vessel forming pattern. When the photocatalyst-containing layer side substrate having photocatalyst-containing layer side light-shielding portion is used in this way, at the time of irradiating energy, it is not necessary to use any photomask or to carry out drawing irradiation with a laser light. Since alignment of the photomask and the photocatalyst-containing layer side substrate is not necessary, process can be made simple. Further, since expensive device for drawing irradiation is also not necessary, it is advantageous in costs.

The photocatalyst-containing layer side light shielding portion of the photocatalyst-containing layer side may be formed between the base body and the photocatalyst-containing layer, or may be formed on the photocatalyst-containing layer. Moreover, it may be formed on the surface side of the base body contrary to the side where the photocatalyst-containing layer is formed.

A forming method of the photocatalyst-containing layer side light shielding portion is not particularly limited, since it is appropriately selected and used corresponding to the property of the forming surface of the photocatalyst-containing layer side light shielding portion and the shielding property against the energy which is required, and it can be made similar to the light shielding portion provided on the base material explained in the first embodiment, the detailed explanation is not repeated here. Moreover, in the case where the photocatalyst-containing layer side light shielding portion is formed between the base body and the photocatalyst-containing layer, a primer layer may be formed between the photocatalyst-containing layer side light shielding portion and the photocatalyst-containing layer. As the primer layer, for example, a primer layer described in JP-A No. 2002-173205 can be used.

b. Forming Method of Cell Adhesion-Inhibiting Portion

Next, a forming method of a cell adhesion-inhibiting portion in the present embodiment will be explained below. In the present embodiment, for example, as shown in FIGS. 4A and 4B, the blood vessel cell adhesion layer 15 formed on the base material 11 and the photocatalyst-containing layer 22 of the photocatalyst-containing layer side substrate 21 are disposed at a predetermined interval, and the energy 14 is irradiated from a predetermined direction using such as the photomask 13 (FIG. 4A). Owing to this, the blood vessel cell adhesive material in the area where the energy irradiated is decomposed or denatured and the cell adhesion-inhibiting portion 3 not having the adhesive properties with the blood vessel cell is formed in the cell adhesion portion 2 (FIG. 4B). At this time, as for the cell adhesion-inhibiting portion, for example, in the case where the blood vessel cell adhesive material is decomposed by the action of the photocatalyst accompanying with the energy irradiation, the small amount of the blood vessel cell adhesive material is contained in the cell adhesion-inhibiting portion, the decomposed material of the blood vessel cell adhesive material and the like is contained, or the blood vessel cell adhesion layer is completely decomposed and removed to expose the base material. Moreover, in the case where the blood vessel cell adhesive material is denatured by the action of the photocatalyst accompanying with the energy irradiation, the denatured material and the like is contained in the cell adhesion-inhibiting portion.

The above-mentioned wording "disposing" means that the layers are disposed in the state that the action of the photocatalyst can substantially work to the surface of the blood vessel cell adhesion layer, and include not only the state that the two layers actually contact each other, but also the state that the photocatalyst-containing layer and the blood vessel cell adhesion layer are disposed at a predetermined interval. The dimension of the interval is preferably 200 μm or less.

In this embodiment, the dimension of the interval is more preferably in the range of 0.2 μm to 10 μm, even more preferably in the range of 1 μm to 5 μm, since the precision of the pattern to be obtained becomes very good and further the sensitivity of the photocatalyst becomes high so as to make good efficiency of the decomposition or denaturation of the blood vessel cell adhesive material in the blood vessel cell adhesion layer. This range of the interval dimension is particularly effective for the blood vessel cell adhesion layer which is small in area, wherein the interval dimension can be controlled with a high precision.

Meanwhile, in the case of treating the blood vessel cell adhesion layer having large area, for example, 300 mm×300 mm or more in size, it is very difficult to make a fine interval as described above between the photocatalyst-containing layer side substrate and the blood vessel cell adhesion layer without contacting each other. Accordingly, when the blood vessel cell adhesion layer has a relatively large area, the interval dimension is preferably in the range of 10 to 100 μm, more preferably in the range of 50 to 75 µm. By setting the interval dimension in the above range, the following problems will not occur that: deterioration of patterning precision, such as blurring of the pattern; or the sensitivity of the photocatalyst deteriorates so that the efficiency of decomposing or denaturing the blood vessel cell adhesive material is also deteriorated. Further, there is an advantageous effect that the blood vessel cell adhesive material is not unevenly decomposed or denatured.

When energy is irradiated onto the blood vessel cell adhesion layer having a relatively large area as described above, the dimension of the interval, in a unit for positioning the photocatalyst-containing layer side substrate and the blood vessel cell adhesion layer inside the energy irradiating device, is preferably set in the range of 10 µm to 200 µm, more preferably in the range of 25 µm to 75 µm. The setting of the interval dimension value into this range makes it possible to dispose the photocatalyst-containing layer side substrate and the blood vessel cell adhesion layer without causing a large deterioration in patterning precision or of sensitivity in the photocatalyst, and without bringing the substrate and the layer into contact with each other.

When the photocatalyst-containing layer and the surface of the blood vessel cell adhesion layer are disposed at a predetermined interval, active oxygen species generated from oxygen and water by action of the photocatalyst can easily be released. In other words, if the interval between the photocatalyst-containing layer and the blood vessel cell adhesion layer is made narrower than the above-mentioned range, the active oxygen species are not easily released, so, as to make the rate for decomposing or denaturing the blood vessel cell adhesive material unfavorably small. If the two layers are arranged at an interval larger than the above-mentioned range, the generated active oxygen species do not reach the blood vessel cell adhesion layer easily. In this case also, the rate for decomposing or denaturing the blood vessel cell adhesive material may become unfavorably small.

The method for disposing the photocatalyst-containing layer and the blood vessel cell adhesion layer to make such a very small interval evenly therebetween is, for example, a method of using spacers. The use of the spacers in this way makes it possible to make an even interval. At the same time, the action of the photocatalyst does not work onto the surface of the blood vessel cell adhesion layer in the regions which the spacers contact. Therefore, when the spacers are rendered to have a pattern similar to that of the cell adhesion portions, the blood vessel cell adhesive material only inside regions where no spacers are formed can be decomposed or denatured so that highly precise cell adhesion-inhibiting portions can be formed. The use of the spacers also makes it possible that the active oxygen species generated by action of the photocatalyst reach the surface of the blood vessel cell adhesion layer, without diffusing, at a high concentration. Accordingly, highly precise cell adhesion-inhibiting portion can be effectively formed.

In this embodiment, it is sufficient that such a disposed state of the photocatalyst-containing layer side substrate is maintained only during the irradiation of energy.

The energy irradiation (exposure) mentioned in this embodiment is a concept that includes all energy ray irradiation that can decompose or denature the blood vessel cell adhesive material by the action of the photocatalyst upon irradiation with energy, and is not limited to light irradiation.

The kind and other properties of the energy irradiated are the same as those explained in the first embodiment, thus the detailed explanation thereof is omitted here.

The energy irradiation that is carried out via a photomask in this embodiment, when the above-mentioned base material is transparent, may be carried out from either direction of the base material side or a photocatalyst-containing layer side substrate. On the other hand, when the base material is opaque, it is necessary to irradiate energy from a photocatalyst-containing layer side substrate.

(6) Sixth Embodiment

Still further, as a six embodiment, the cell culturing layer is a blood vessel cell adhesion-inhibiting layer having the adhesion-inhibiting properties which inhibits adhesion to the blood vessel cell containing a blood vessel cell adhesive-inhibiting material decomposed or denatured by the action of the photocatalyst accompanying with the energy irradiation; and it is a case where for example, the cell adhesion portion is formed by decomposing or denaturing the blood vessel cell adhesion-inhibiting material by disposing the blood vessel cell adhesion layer and the photocatalyst-containing layer containing a photocatalyst opposed to each other and by irradiating the energy using such as a photomask having the light shielding portion in a pattern form of the blood vessel formation pattern.

In the present embodiment, since the blood vessel cell adhesion-inhibiting material decomposed or denatured by the action of the photocatalyst accompanying with the energy irradiation is contained in the blood vessel cell adhesion-inhibiting layer, the blood vessel cell adhesion-inhibiting material in the blood vessel cell adhesion-inhibiting layer is decomposed or denatured and the cell adhesion portion having the adhesive properties with the blood vessel cell can be formed by disposing the blood vessel cell adhesion-inhibiting layer and the photocatalyst-containing layer opposed to each other and by irradiating the energy in a pattern form of the blood vessel formation pattern by means of the action of the photocatalyst in the photocatalyst-containing layer. At this time, concerning with the area where the energy is not irradiated, since the blood vessel cell adhesion-inhibiting material remains, it can be made the area not having the adhesive properties with the blood vessel cell, and it can be used as a cell adhesion-inhibiting portion.

Here, the fact that the blood vessel cell adhesion-inhibiting material is decomposed or denatured means that the blood vessel cell adhesion-inhibiting material is not contained, or the small amount of the blood vessel cell adhesion-inhibiting material is contained when it is compared to the amount of the blood vessel cell adhesion-inhibiting material contained in the cell adhesion-inhibiting portion. For example, in the case where the blood vessel cell adhesion-inhibiting material is decomposed by the action of the photocatalyst accompanying with the energy irradiation, the small amount of the blood vessel cell adhesion-inhibiting material is contained, the decomposed material of the blood vessel cell adhesion-inhibiting material or the like is contained, or the blood vessel cell adhesion-inhibiting material is completely decomposed and the photocatalyst-containing layer is exposed. Moreover, in the case where the blood vessel cell adhesion-inhibiting material is denatured by the action of the photocatalyst accompanying with the energy irradiation, the denatured material or the like is contained in the cell adhesion portion. In the present embodiment, it is preferable that the cell adhesion material having the adhesive properties with the blood vessel cell is contained in the cell adhesion portion at least after the energy has been irradiated. It is because owing to this, that the adhesive properties with the blood vessel cell of the cell adhesion portion can be made higher, and it becomes possible that the blood vessel cell is adhered to only the cell adhesion portion in a highly fine process.

The blood vessel cell adhesion-inhibiting layer used in the present embodiment is similar to the blood vessel cell adhesion-inhibiting layer explained in the fourth embodiment; and the photocatalyst-containing layer side substrate, the disposition, a method of irradiating the energy and the like are similar to those explained in the fifth embodiment. Accordingly, the detailed explanations are not repeated here.

4. Blood Vessel Cell Culturing Process

Next, the process for culturing a blood vessel cell in the present invention will be explained below. The process for culturing a blood vessel cell in the present invention is a process in which the blood vessel cells are adhered to the above-described cell adhesion portion in a pattern of the of blood vessel cell culturing pattern, cultured and made into a tissue. According to the present process, the blood vessels can be formed by adhering the blood vessel cells to the cell adhesion portion and making into the tissue.

The blood vessel cells used in the present process are blood vessel cells which are cultured and organize the blood vessels, and these means vascular endothelial cells, pericyte, smooth muscle cells, vascular endothelial precusor cell, smooth muscle precusor cell obtained from the respective living organisms, particularly from human and animals, and particularly, vascular endothelial cells and the like can be used. Plural kinds of cells can be co-cultured such as co-culture of vascular endothelial cells and pericytes or co-culture of vascular endothelial cells and smooth muscle cells.

Moreover, as a method of adhering the blood vessel cells to the cell adhesion portion, if it is a method of being capable of adhering the blood vessel cells only to the cell adhesion portion in a pattern of the blood vessel cell culturing pattern having the cell adhesion portion and the cell adhesion-inhibiting portion, it is not particularly limited. For example, it may be a method of adhering the blood vessel cells by an ink jet printer or a manipulator, however, the following method is generally used: a method in which after the blood vessel cells were adhered to the cell adhesion portion by disseminating the blood vessel cell suspension, the blood vessel cells on the cell adhesion-inhibiting portion which has been unnecessary is washed with phosphate buffer, and the blood vessel cells are removed. As the above-described method, for example, the method described in the reference document "Spatial distribution of mammalian cells dictated by material surface chemistry", Kevin E. Healy, et al, Biotech. Bioeng. (1994), p. 792 can be used.

Moreover, in the present invention, blood vessels can be formed by make the blood vessel cells in contact with the anchorage material for promoting to make the blood vessel cells into the blood vessels such as Matrigel as it is in a form of the blood vessels adhered to the blood vessel cell adhesion portion. Still further, it is also possible that the blood vessel cells are transferred on the tissue to be contacted in a desired form and the blood vessels are artificially formed by making the tissue to be contacted as an anchorage by contacting directly the base material with the blood vessel cells adhered to the blood vessel cell adhesion portion with the tissue such as skin.

Furthermore, after it was formed in a targeted pattern on the blood vessel cell adhesion portion, artificial blood vessels can be formed directly on the cell culturing layer by adding on the culture medium the growth factor for promoting to make the blood vessel cells into blood vessels such as bFGF and VEGF. To stably perform the formation of the blood vessels of the blood vessel cells, however, it is desired that the former method using an anchorage is applied.

B. Method of Manufacturing Artificial Tissue

Next, a method of manufacturing an artificial tissue of the present invention will be explained below. A method of manufacturing an artificial tissue of the present invention is characterized in that it uses artificial blood vessels manufactured according to the "A method of manufacturing an artificial blood vessel". According to the present invention, since the artificial blood vessels manufactured by the above-described method of manufacturing are used, it can be made into an artificial tissue having the blood vessels formed in a similar pattern form with the blood vessel pattern existing in the living tissues. Therefore, it becomes possible that the nutrients are supplied from these artificial vessels to the respective tissues in the artificial tissues manufactured by the present invention, and it can be made an artificial tissue that can be used in a variety of uses.

As a method of manufacturing an artificial tissue in the present invention, for example, if it has the above-described artificial blood vessels, it is not particularly limited. For example, it can be formed by the blood vessels existing in the living body and the other cells or the like to be an organ such as kidney, or liver and a variety of kinds of organs.

As a method of manufacturing an artificial tissue in the present invention, for example, a method in which cells other than the blood vessels forming the artificial tissue are cultured on the culture medium and made into a tissue and the blood vessels are disposed on these cells, a method in which the above-described artificial blood vessels are disposed on the culture medium, the above-described cells are cultured on the culture medium and made into a tissue are listed. In the present invention, it may be made into an artificial tissue by combining a plurality of the layers formed in this way.

Moreover, as a cell used at this time, if it is a cell that becomes active receiving the supply such as oxygen and nutrients from the above-described blood vessels and is capable of constituting the artificial tissue, it is not particularly limited. For example, cell species having the metabolic functions such as hepatic parenchymal cell, and Langerhans' cell, cell species of information transmission system such as brain cells and nerve cells are listed. As the above-described cell used for manufacturing an artificial tissue of the present invention, it is not limited to one species, and may be cells by combining a plurality of kinds of cells.

The culture medium for culturing the above-described cell or the like is appropriately selected by the targeted cell. Since the culture medium generally used for the culturing cells can be used, the detailed explanation is not repeated here.

C. Photomask

Next, a photomask of the present invention will be explained below. A photomask of the present invention is characterized in that it has a blood vessel pattern comprising a two-dimensional pattern constituted by the line width in which a vascular endothelial cell is a tubular form.

According to the present invention, since a photomask has a pattern comprising the line width in which a vascular endothelial cell is in a tubular form, the blood vessels formed in the above-described pattern can be formed using this photomask, for example, by patterning the blood vessel cell adhesion layer into the pattern form and culturing a vascular endothelial cell on the cell adhesion layer and making it in a tubular form. Therefore, the blood vessels having a variety of patterns can be formed using this photomask, and the blood vessels having a pattern similar to the form of the blood vessels of the living tissue can be formed by utilizing it, for example, for exposure of the cell culturing layer as explained in the process for forming a blood vessel cell culturing pattern of the above-described "A method of manufacturing an artificial blood vessel".

Here, as for the line width in which the vascular endothelial cell is in a tubular form, although it depends upon the kind of a vascular endothelial cell, it is preferably to be usually in the range from 20 μm to 100 μm, and more preferably to be in the range from 40 μm to 80 μm, and particularly preferably to be in the range from 50 μm to 70 μm. By making it in the above-described ranges, it is because a vascular endothelial cell can be efficiently made into a tubular form. In the present invention, at the time when it is exposed by utilizing the photomask, the pattern of the pattern might be enlarged or reduced and to be exposed. In this case, it is preferable that the line width of the above-described pattern formed on the photomask is not limited in the above-described ranges, however, it is preferable that the line width of the photomask is determined so that the line width of the blood vessel pattern of the projected image is in the above-described range.

Moreover, in a photomask of the present invention, for example, it may be available that the pattern of the blood vessels is formed to be the light shielding portion, and it may be also available that it is formed such that the pattern of the blood vessels becomes the opening portion.

Still further, as for the blood vessel pattern comprising a two-dimensional pattern constituted with the above-described line width, if it is a blood vessel pattern represented in two-dimension, it is not particularly limited. For example, it can be made a blood vessel pattern observed on a predetermined cross-section of the living tissue. In the case where the pattern of the blood vessels is made in a blood vessel pattern of the living tissue, it may be formed such that the blood vessel pattern of the living tissue and the pattern formed on the photomask are the same to each other. Alternatively, for example, in order to make the formation of the blood vessels easy, the pattern of the respective blood vessels formed on the photomask may be adjusted. Still further, it may be the pattern in which the necessary form of the blood vessels has been added, deleted and so on. As for the above-described adjustment, for example, it can be made the adjustment as explained in the process for adjusting the blood vessel formation pattern of "A method of manufacturing an artificial blood vessel".

The above-described living tissues denote to tissues existing in the living body and these are tissues formed with the blood vessel cells and the other cells and these are organs. For example, they include an organ such as kidney or liver and the respective kinds of organs including blood vessels such as ocular fundus or skin.

In the present invention, if it is possible that the photomask as described above is formed, the method is not particularly limited. Since a forming method of a photomask, and its materials or the like are similar to the method or the material used in a general photomask, the detailed explanation is not repeated here.

D. Artificial Blood Vessel

Next, artificial blood vessel of the present invention will be explained below. Artificial blood vessels of the present invention is characterized in that it has a blood vessel pattern formed by the two-dimensional pattern constituted with the line width in which a vascular endothelial cell is in a tubular form.

According to the present invention, since the artificial blood vessel is formed by the above-described pattern, for example, it can be made an artificial blood vessel having a pattern similar to the blood vessels in the living tissue and it can be made into the blood vessels for playing the functions similar to the blood vessels existing in the living tissue by for example disposing it at the infarct site of the micro blood vessels or in an artificial tissue.

Here, as for the line width in which a vascular endothelial cell is in a tubular form, although it depends upon the kind of a vascular endothelial cell constituting the artificial blood vessel of the present invention, it is usually in the range from 20 μm to 100 μm, preferably in the range from 40 μm to 80 μm, and particularly preferably in the range from 50 μm to 70 μm. It is because owing to this, a vascular endothelial cell is in a tubular form, and the formation of artificial blood vessel of the present invention becomes easy.

Moreover, as for a blood vessel pattern formed by a two-dimensional pattern constituted by the above-described line width, it can be made into a blood vessel pattern in a tubular form by culturing a vascular endothelial cell culture in a pattern form of the above-described pattern form. For example, it can be made into a blood vessel pattern observed on a predetermined cross-section of the living tissue. At this time, the above-described blood vessel pattern can be made into the pattern form same to the blood vessels existing in the living tissue, however, for example, it can be also made into a pattern in which the form of the blood vessel such as the diameter or the position of the blood vessel existing in the living tissue has been adjusted; or a pattern in which the blood vessel for introducing the blood from the blood vessel existing in the artificial tissue or the living body, or the blood vessels for exhausting has been formed. As for the above-described adjustment, for example, it can be made the adjustment as explained in the process for adjusting a blood vessel formation pattern of "A method of manufacturing an artificial blood vessel".

The above-described living tissues denote to tissues existing in the living body and these are tissues formed by the blood vessel cells, the other cells or the like. For example, these include an organ such as kidney or liver, and the respective kinds of organs including blood vessels such ocular fundus, or skin. In the present invention, as a forming method of the above-described artificial blood vessels, it could be formed by the method explained in the above-described "A method of manufacturing an artificial blood vessel", and as for the material used in the formation of artificial blood vessels of the present invention, it can be made material similar to the above-described material. Accordingly, the detailed explanation is not repeated here.

E. Artificial Tissue

Next, an artificial tissue of the present invention will be explained below. An artificial tissue of the present invention is characterized in that it has the above-described artificial blood vessels in addition to the parenchymal cell having the desired functions derived from the organ. In the case where the block of the cells only comprises parenchymal cell of the organ, since the carrying of nutrients and metabolic decomposition product is not performed, the cell existing within the internal site is necrotized. According to the present invention, since it becomes possible that the tissue having the artificial blood vessel is formed in addition to the parenchymal cell of the organ, it can be made function without necrotizing the tissue. Therefore, according to the present invention, it can be made into an artificial tissue that can be used for a variety of uses.

As for an artificial tissue of the present invention, if it is an artificial tissue having the above-described blood vessel, it is not particularly limited, however, it can be made into a tissue formed by the blood vessels existing in the living body, the other cells or the like. For example, it can be made into organs such as kidney or liver, and a variety of kinds of organs such as ocular fundus or skin.

As for a method of manufacturing the artificial tissue, since it can be made into a method similar to the method explained in the above-described "B. Method of manufacturing artificial tissue", the detailed explanation is not repeated here.

F. Blood Vessel Cell Culturing Pattern Base Material

Next, a blood vessel cell culturing pattern base material of the present invention will be explained below. A blood vessel cell culturing pattern base material of the present invention comprises: a base material; a cell culturing layer formed on the base material and having a pattern comprising a cell adhesion portion having adhesive properties with a blood vessel cell and a cell adhesion-inhibiting portion for inhibiting adhesion with the blood vessel cell; and a blood vessel cell adhered to the cell adhesion portion, characterized in that the cell adhesion portion is formed in a blood vessel pattern comprising a two-dimensional pattern constituted with a line width in which a vascular endothelial cell is in a tubular form.

As shown in FIG. 5, A blood vessel cell culturing pattern base material of the present invention has the base material 11, the cell culturing layer 1 having a pattern comprising the cell adhesion portion 2 and the cell adhesion-inhibiting portion 3 formed on the base material 11 in a predetermined pattern form, and the blood vessel cell 4 adhered to the cell adhesion portion 2.

According to the present invention, since the cell adhesion portion has been formed on the cell culturing layer in a predetermined pattern form and the area other than that is made as the cell adhesion-inhibiting portion, blood vessel cell can be cultured in a finely processed pattern only on the cell adhesion portion. Owing to this, it can be made into blood vessel cell culturing pattern base material capable of forming blood vessels in a targeted finely processed pattern. Still further, since the line width of the cell adhesion portion has been made into a line width such that a vascular endothelial cell is in a tubular form, it can be made into a blood vessel cell culturing pattern base material capable of efficiently forming the artificial blood vessel by easily making the cultured blood vessel cell into a tubular form.

Here, as for the line width in which a vascular endothelial cell is in a tubular, it is a line width in which the blood vessel cell cultured on the cell adhesion portion and made into the tissue becomes in a tubular form. Specifically, although it depends upon the kind of blood vessel the cell or the like, it is usual in the range from 20 μm to 100 μm, more preferably in the 40 μm to 80 μm and particularly preferably in the range from 50 μm to 70 μm. It is because owing to this, artificial blood vessels are easily formed with the blood vessel cells cultured on the cell adhesion portion.

Moreover, as for a blood vessel pattern comprising a two-dimensional pattern constituted with the above-described line width, if it is a blood vessel pattern represented in two-dimension, it is not particularly limited. For example, it can be made a blood vessel pattern observed on a predetermined cross-section of the living tissue. At this time, the form of the above-described pattern form may be the same with that of the blood vessels existing in the living tissue. Alternatively, for example, it can be also made a pattern in which a form of the blood vessel such as the diameter or position of the blood vessels existing in the living tissue has been adjusted, or a pattern in which the blood vessels for introducing the blood from the blood vessels existing in the artificial tissue or the living body or the blood vessels for exhausting have been formed.

Here, as for a base material used for the blood vessel cell culturing pattern base material of the present invention, a cell culturing layer having the cell adhesion portion and the cell adhesion-inhibiting portion and blood vessel cells, they can be similar to those explained in the item of the above-described "A method of manufacturing an artificial blood vessel". Accordingly, the detailed explanation is not repeated here.

If the blood vessel cell culturing pattern base material as described above is used, the following a vascular endothelial cell pattern base material characterized in can be obtained; the base material is comprising the base material and a vascular endothelial cell provided on the base material in such a way that can be peeled off, and the vascular endothelial cell has been formed with the line width becoming in a tubular form in a pattern in which the blood vessel network has been expressed in two-dimension. In the above-described vascular endothelial cell pattern base material, since a vascular endothelial cell formed in a predetermined pattern form has been provided in a way that can be peeled off, the vascular endothelial cell is peeled off from the vascular endothelial cell pattern base material, and it can be used for a variety of uses such as artificial tissue.

In the base material of a vascular endothelial cell with which the above-described vascular endothelial cell can be peeled off, as a culture base, the vascular endothelial cell pattern base material which does not damage a vascular endothelial cell and is capable of peeling off a vascular endothelial cell is used. As the above-described culture base, a culture base having a surface capable of holding the cell by a weak adhesive force is listed. Specifically, a culture base in which the plasma treatment for adhering the cell has been provided to a polystyrene base material, a culture base in which a material having the cell adhesion-inhibiting properties such as 2-methacryloyloxyethyl phosphorylcoline or fluoroalkylsilane has been slightly introduced on the surface of the base material are listed as examples. As the above-described method of introducing small amount, a method of decomposing by a UV treatment, an ozone treatment, a plasma treatment after the material has been sufficiently introduced into the base material by an absorbing treatment or the like, or a method of coating a thin layer with a solution thinly resolved in a solution and the like are listed. As for the rate of introduction, it is different depending upon the kind of cell to be adhered and the kind of a material which is introduced into the base material, therefore, it is necessary to be adjusted.

Moreover, temperature-responsive polymer materials such as poly-N-isopropylacryl amide, in which a material that is hydrophobic in the environment at the temperature of the phase transition temperature or higher and have cell adhesion properties, while it is hydrophilic at the temperature of the phase transition temperature or lower and lose the cell adhesion properties, has been polymerized on the base material of the high molecular polymer, a glass or the like, can be also used.

The present invention is not limited to the above-described embodiment. The above-described embodiments have been exemplified, and any embodiment which has the constitution substantially the same with the technical idea described in the scope of the present invention and exerts a similar action effect is included in the technical scope of the present invention.

EXAMPLES

Hereinafter, Examples are shown and the present invention will be further specifically explained below.

Example 1

Photomask

The photograph of human ocular fundus was shot and the blood vessel image in the living body was obtained. This image was installed by a scanner into the computer. Next, the image installed was binarized by Scion Image, the noise was removed by median filter treatment, and the edge enhancement was performed. The blood vessel formation pattern in the living body adjusted in the most suitable width of the blood vessel cell adhesion for the blood vessel formation was prepared by extracting the line pattern from the binarized blood vessel image, victorizing and further integrating the line width into 60 μm.

Further, the prepared blood vessel formation pattern was vectrized again and, similar to the usual photomask preparation procedure, a photomask having a desired pattern was prepared by a laser drawing machine. At the time when the photomask was prepared, the blood vessel portion was made a transparent portion, the portion other than the blood vessel was made the light shielding portion.

Example 2

Blood Vessel Cell Culturing Pattern Base Material

Mixed for 12 hours were 1.5 g of fluoroalkylsilane TSL8233 (GE Toshiba Silicone Co., Ltd.), 5.0 g of tetramethoxysilane TSL8114 (GE Toshiba Silicone Co., Ltd.), 2.4 g of $5.0 \times 10^{-3}$ NHCl, and the resultant was diluted into 10-fold with isopropyl alcohol. Next, 2.0 g of this solution was coated on the base material of soda glass having the size of 10 cm×10 cm using a spin coater at 1000 rpm for 5 seconds, the base material was dried at 150° C. for 10 minutes and made it into a blood vessel cell adhesion-inhibiting layer.

Next, 3.0 g of titanium oxide sol solution which has been diluted into 3-fold with isopropyl alcohol (Ishihara Sangyo Kaisha, Ltd. STK-03) was made composition for the photocatalyst-containing layer. The composition for the photocatalyst-containing layer was coated at 700 rpm for 3 seconds using a spin coater on the pattern surface of the quarz photomask prepared by a method similar to Example 1, and a photomask having a transparent photocatalyst-containing layer was prepared by performing the drying treatment at 150° C. for 10 minutes.

These were disposed such that the interval between the surface of the photocatalyst-containing layer of the photomask and the surface of the blood vessel cell adhesion-inhibiting layer of the base material becomes 3 μm, ultraviolet ray exposure was performed for a predetermined time period at 4 $J/cm^2$ using a mercury lamp (wavelength: 365 nm) from the photomask side, and a cell culturing pattern having the cell adhesion portion having the width of 60 μm was obtained.

<Blood Vessel Cell Culturing Process>

As a culture cell, a vascular endothelial cell derived from bovine carotid artery (see Onodera M, Morita I, Mano Y, Murota S: Differential effects of nitric oxide on the activity of prostaglandin endoperoxide h synthase-1 and -2 in vascular endothelial cells, Prostag Leukotress 62: 161-167, 2000) of 5-generation to 20-generation of the passage number were used.

A vascular endothelial cell derived from bovine carotid artery in the confluent state in 10 cm dish was treated with 0.05% tripsin-EDTA, and peeled off. The number of cells was examined using Coulter Counter ZM (trademark), and made it $10^6$ pieces/mL. The base material having the cell culturing pattern previously prepared was sterilized using an autoclave. The base material with the above-described cell culturing pattern formed has been inputted in the culture dish (Heraeus Quadriprem (trademark) 76×26 mm, 1976 $mm^2$) containing the culture solution (5% bovine fetal serum containing MEM culture medium), the above-described endothelial cells were disseminated at $10^6$ pieces/5 mL per 1 well, and incubated for 24 hours using $CO_2$ cell culture device. Owing to this, a blood vessel cell culturing pattern base material in which blood vessel cells were adhered in the cell culturing pattern form was obtained.

Example 3

To the blood vessel cell culturing pattern base material to which the blood vessel cells were adhered in a pattern form prepared in Example 2, 2 mL of GFR matrigel (manufactured by Becton, Dickinson and Company) as an anchorage for making blood vessel tissue of the blood vessel cells was made in contact with the blood vessel cell adhesion surface side of the base material, and heated at 37° C. After the gel was solidified, the base material and the gel were inputted in the $CO_2$ cell culture device in the presence of the culture solution, and the blood vessel cells were made into a tissue.

After 24 hours, when the blood vessel tissue prepared was observed by a retardation microscope, and after cell staining, immunostaining were performed, it was observed by a fluorescence microscope, the formation of a tubular tissue having an internal cavity was admitted.

Example 4

The blood vessel cell culturing pattern base material to which the blood vessel cells have adhered in a pattern form by a similar procedure with Example 2 was immersed on the culture medium in which carbocyanine fluorescence pigment (DiI, manufactured by Invitrogen, Co., Ltd.) was resolved at the concentration of 10 μg/mL with respect to 5% bovine fetal serum containing MEM culture medium, and cultured at 37° C. for one hour. Subsequently, the blood vessel cell culturing pattern base material was returned to 5% bovine fetal serum containing MEM culture medium.

(Cell Introduction to Living Tissue)

The immunodeficient mouse was anesthetized, the back was cut, and the base material to which the prepared blood vessel cells are aligned and adhered was subcutaneously transplanted. The transplanted portion was sutured. The transplanted portion was cut again at 3 day after it was sutured, then, FITC-Dextran resolved solution was injected from the tail vein and the blood was stained. The sacrificial death operation was performed to the mouse and DiI and FITC of the transplanted tissue portion were observed by a confocal laser scanning microscope.

As a result of the observation, the facts that the fluorescence-labeled blood vessel cells formed the structure of the blood vessels in the transplanted tissue portion and the blood containing a fluorescence pigment communicated within the structure of the blood vessels were admitted.

Example 5

With respect to the Schale in which 0.5 mL of matrigel was dropped, the cell adhesion surface of the blood vessel cell culturing pattern base material to which the blood vessel cells have adhered in a pattern prepared in Example 2 was superposed so that the cell adhesion surface is made in contact to the gel, and the gel was heated to 37° C. and solidified. The base material and the gel were inputted in the $CO_2$ cell culture device in the presence of the culture solution and cultured for 24 hours, and the blood vessel cells were made into a tissue. After the blood vessels were formed, the base material was peeled off from the gel.

In parallel to the above-described operation, the mouse liver parenchymal cell was collected, after it was stained with 10 μg/mL of carbocyanine fluorescence pigment (DiO, manufactured by Invitrogen, Co., Ltd.), it was returned to 5% bovine fetal serum containing MEM culture medium, and fluorescence stained mouse liver parenchymal cell was obtained.

After the liver parenchymal cell was embedded in the gel by disseminating the above-described fluorescence stained liver parenchymal cell on the gel having the artificial blood vessels, inputting the fluorescence stained liver parenchymal cell in the $CO_2$ cell culture device and culturing it for 24 hours, the tissue was peeled off from the Schale using tweezers and a tissue piece comprising a gel having the artificial blood vessels and liver parenchymal cell was prepared.
(Evaluation of Tissue)

The immunodeficient mouse was anesthetized, abdominal portion was cut, ⅓ of the liver was removed, and made it into a liver function failure model. Next, the tissue piece prepared in the above-described operation was transplanted in the liver portion of the mouse. The transplanted portion was sutured and the evaluation of the liver functions was performed by cholinesterase evaluation after 14 days, as a result of this, it was admitted that the liver functions were recovered to the same level prior to the removal of the liver.

Furthermore, the liver function transplanted portion was cut again, and the transplanted tissue was observed using a confocal laser scanning microscope. The transplanted liver parenchymal cell was observed by the observation at 480 nm of the excitation wavelength. Moreover, it was admitted that capillary blood vessels have been formed as a vascular endothelial cell was previously patterned by the observation at 530 nm of the excitation wavelength.

Comparative Example 1

The immunodeficient mouse was anesthetized, the abdominal portion was cut, ⅓ of the liver was removed, and made it into a liver function failure model. The transplanted portion was sutured again without transplanting the tissue pieces, the evaluation of the liver functions was performed by cholinesterase evaluation after 14 days. As a result of this, it was admitted that the liver functions remained was about 40% comparing to the prior to the removal of the liver.

Comparative Example 2

The mouse liver parenchymal cell was collected, after it was stained with 10 μg/mL of carbocyanine fluorescence pigment (DiO, manufactured by Invitrogen, Co., Ltd.), it was returned to 5% bovine fetal serum containing MEM culture medium, and fluorescence stained mouse liver parenchymal cell was obtained.

After the liver parenchymal cell was embedded in the gel by disseminating the above-described fluorescence stained liver parenchymal cell on the matrigel not having the blood vessel cells, inputting the fluorescence stained liver parenchymal cell in the $CO_2$ cell culture device and culturing it for 24 hours, the tissue was peeled off from the Schale using tweezers and a gel tissue piece comprising with the liver parenchymal cell embedded was prepared.
(Evaluation of Tissue)

The immunodeficient mouse was anesthetized, abdominal portion was cut, ⅓ of the liver was removed, and made it into a liver function failure model. Next, the tissue piece prepared in the above-described operation was transplanted in the liver portion of the mouse. The transplanted portion was sutured and the evaluation of the liver functions was performed by cholinesterase evaluation after 14 days, as a result of this, it was admitted that the liver functions remained was about 40% comparing to the prior to the removal of the liver.

Furthermore, the liver function transplanted portion was cut again, and the transplanted tissue was observed using a confocal laser scanning microscope. When the transplanted liver parenchymal cell was observed by the observation at 480 nm of the excitation wavelength, it was admitted that the transplanted liver parenchymal cell was scarcely seen and almost all of the transplanted cells were necrotized.

What is claimed is:
1. A blood vessel cell culturing pattern system comprising:
a) a base material;
b) a cell culturing layer formed on the base material and having a pattern comprising a cell adhesion region and cell adhesion-inhibiting region; and
c) at least one blood vessel cell adhered to the cell adhesion region;
wherein the pattern of the cell culturing layer is a two-dimensional blood vessel pattern;
wherein at least a portion of the cell adhesion region has a width greater than 100 μm, and within the cell adhesion regions having a width greater than 100 μm there is formed an auxiliary pattern of fine cell adhesion-inhibiting areas having a width of 0.5 to 10 μm.

2. The blood vessel cell culturing pattern system of claim 1, wherein within the auxiliary pattern the fine cell adhesion-inhibiting areas have a width of 1-5 μm.

3. The blood vessel cell culturing pattern system of claim 1, wherein the two-dimensional pattern of the cell culturing layer comprises a branching pattern.

4. The blood vessel cell culturing pattern system of claim 1, wherein the blood cell is a vascular endothelial cells.

5. The blood vessel cell culturing pattern system of claim 4, wherein multiple vascular endothelial cells are present on the cell culturing layer and form a blood vessel tissue in the pattern of the cell adhesion region.

6. The blood vessel cell culturing pattern system of claim 5, wherein the blood vessel tissue can be removed from the base material without damaging the vascular endothelial cells.

7. The blood vessel cell culturing pattern system of claim 1, wherein the base material is a polystyrene base material.

8. The blood vessel cell culturing pattern system of claim 1, wherein the cell adhesion-inhibiting region contains a cell adhesion-inhibiting material selected from the group consisting of 2-methacryloyloxyethyl phosphorylcoline, fluoroalkylsilane and combinations thereof.

9. A blood vessel cell culturing pattern system comprising:
a) a base material;
b) a cell culturing layer formed on the base material and having a pattern comprising a cell adhesion region and cell adhesion-inhibiting region; and
c) at least one blood vessel cell adhered to the cell adhesion region;
wherein the pattern of the cell culturing layer is a two-dimensional blood vessel pattern;

wherein at least a portion of the cell adhesion region has a width greater than 100 μm, and within the cell adhesion regions having a width greater than 100 μm there is formed an auxiliary pattern of fine cell adhesion-inhibiting areas having a width sufficiently small so that cell contact between blood vessel cells present on adjoining cell adhesion regions sandwiching the cell adhesion-inhibiting areas is not inhibited.

10. The blood vessel cell culturing pattern system of claim 9, wherein within the auxiliary pattern the fine cell adhesion-inhibiting areas have a width of 1-5 μm.

11. The blood vessel cell culturing pattern system of claim 9, wherein the two-dimensional pattern of the cell culturing layer comprises a branching pattern.

12. The blood vessel cell culturing pattern system of claim 9, wherein the blood cell is a vascular endothelial cells.

13. The blood vessel cell culturing pattern system of claim 12, wherein multiple vascular endothelial cells are present on the cell culturing layer and form a blood vessel tissue in the pattern of the cell adhesion region.

14. The blood vessel cell culturing pattern system of claim 13, wherein the blood vessel tissue can be removed from the base material without damaging the vascular endothelial cells.

15. The blood vessel cell culturing pattern system of claim 9, wherein the base material is a polystyrene base material.

16. The blood vessel cell culturing pattern system of claim 9, wherein the cell adhesion-inhibiting region contains a cell adhesion-inhibiting material selected from the group consisting of 2-methacryloyloxyethyl phosphorylcoline, fluoroalkylsilane and combinations thereof.

* * * * *